United States Patent [19]

Akasaki et al.

[11] Patent Number: 5,047,589
[45] Date of Patent: Sep. 10, 1991

[54] ELECTROPHOTOGRAPHIC LIGHT-SENSITIVE MATERIAL CONTAINING SQUARYLIUM COMPOUND

[75] Inventors: Yutaka Akasaki; Akihiko Tokida; Kaoru Torikoshi; Tooru Ishii; Hidemi Suto; Akira Imai, all of Kanagawa, Japan

[73] Assignee: Fuji Xerox Co. Ltd., Tokyo, Japan

[21] Appl. No.: 278,917

[22] Filed: Dec. 2, 1988

[30] Foreign Application Priority Data

Dec. 4, 1987 [JP] Japan .................... 62-305855
Dec. 4, 1987 [JP] Japan .................... 62-305862
Dec. 4, 1987 [JP] Japan .................... 62-305863
Dec. 4, 1987 [JP] Japan .................... 62-305864
Dec. 4, 1987 [JP] Japan .................... 62-305865
Dec. 4, 1987 [JP] Japan .................... 62-305866

[51] Int. Cl.$^5$ .......................................... C07C 211/00
[52] U.S. Cl. .................................. 564/307; 430/74; 430/76; 430/79
[58] Field of Search ...................... 430/74, 76, 79; 564/307

[56] References Cited

U.S. PATENT DOCUMENTS 4,606,986 8/1986 Yanus et al. ............... 430/74 X
4,624,904 11/1986 Kazmaier et al. ............ 430/74 X
4,746,756 5/1988 Kazmaier et al. ............ 564/307

Primary Examiner—Roland Martin
Attorney, Agent, or Firm—Finnegan, Henderson, Farabow, Garrett, and Dunner

[57] ABSTRACT

An electrophotographic light-sensitive material comprising a conductive support having formed thereon a light-sensitive layer containing a squarylium compound represented by formula (I) or (II)

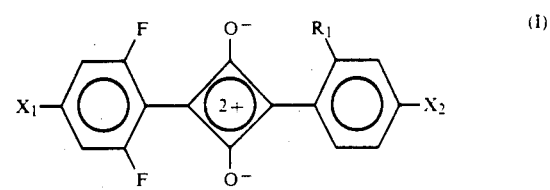

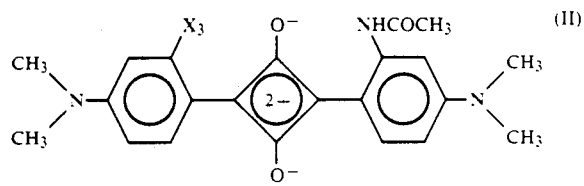

wherein $R_1$ represents a hydrogen atom, a methyl group, a carboxy group, a halogen atom, a trifluoromethyl group, an alkyl or phenyl-substituted carbonamido group, or an alkyl- or phenyl-substituted sulfonamido group; $X_1$ and $X_2$ each represents a group shown by

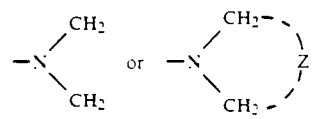

wherein Z represents an atomic group necessary for forming a ring and $R_2$ and $R_3$, each represents an alkyl group having from 1 to 20 carbon atoms, a phenyl group, an unsubstituted benzyl group, or a benzyl group substituted by at least one of an alkyl group having from 1 to 6 carbon atoms, a hydroxy group, an alkoxy group having from 1 to 4 carbon atoms, a halogen atom, a nitro group, a cyano group, an alkoxycarbonyl group having from 2 to 5 carbon atoms, and a trifluoromethyl group); and $X_3$ represents a hydrogen atom, a methyl group, a fluorine atom, or a hydroxy group.

1 Claim, 9 Drawing Sheets

ELECTROPHOTOGRAPHIC LIGHT-SENSITIVE MATERIAL CONTAINING SQUARYLIUM COMPOUND

FIELD OF THE INVENTION

The invention relates to an electrophotographic light-sensitive material, and more particularly to an electrophotographic light-sensitive material having a light-sensitive layer containing a specific squarylium compound.

The invention further relates to a novel squarylium compound for an electrophotographic light-sensitive material and a process of producing the squarylium compound.

Still further, the invention relates to a novel cyclobutenedione derivative which is used for producing the aforesaid squarylium compounds.

BACKGROUND OF THE INVENTION

Hitherto, as for electrophotographic light-sensitive materials, inorganic photoconductive materials such as amorphous selenium, selenium alloys, cadmium sulfide, zinc oxide, etc., and organic photoconductive materials such as polyvinylcarbazole and polyvinylcarbazole derivatives are widely known.

Organic photoconductive materials have the advantages that they are superior in the points of transparency, film-forming property, flexibility, producibility, etc., to inorganic photoconductive materials.

Thus, recently electrophotographic light-sensitive materials using organic photoconductive materials have been variously investigated with keen interest. As these organic photoconductive materials, there are bisazo series pigments, trisazo series pigments, phthalocyanine series pigments, cyanines, pyryliums, etc., in addition to polyvinylcarbazole and the derivatives thereof described above.

However, these organic photoconductive materials are yet inferior to inorganic photoconductors in the points of sensitivity and durability.

Recently, it is reported that certain kinds of squarylium compounds show excellent photoconductive characteristics and can be used for electrophotographic light-sensitive materials as described in JP-A-60-136542, JP-60-142946, JP-60-142947, JP-61-10540, JP-62-450, etc. The term "JP-A" as used herein means an "unexamined published Japanese Patent application".

A squarylium compound is generally synthesized using dichlorobutenedione as a raw material.

In this case, it is known that 3,4-dichloro-3-cyclobutene-1,2-dione (squarylic acid chloride) can form corresponding 3-aryl-4-chloro-3-cyclobutene-1,2-dione by the reaction with an aromatic compound in the presence of Lewis acid as shown by the following reactions (1) and (2) as described in B. R. Green et al, *Synthesis*, 46(1974) and L. A. Wennking et al, *J. Org. Chem.*, 42(7), 1126(1977):

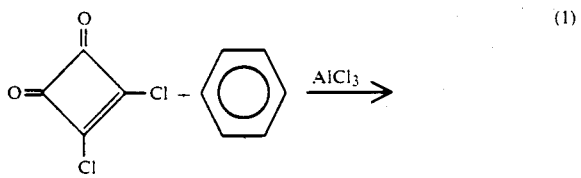

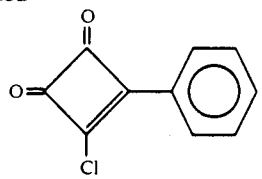

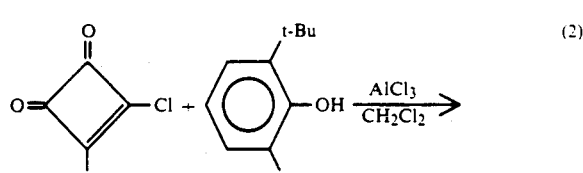

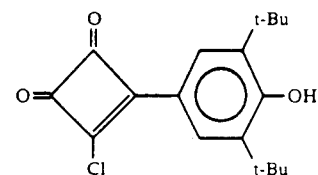

These reactions have a problem in selectivity. In particular, the reaction (2) has a problem of by-producing a 1,2-addition product (yield 3%) shown by formula (3)

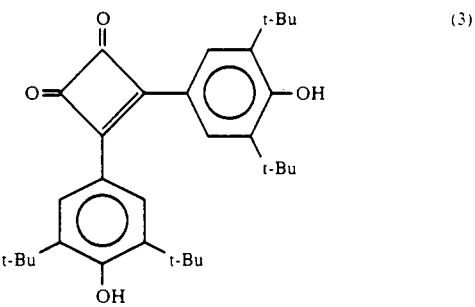

Thus, the inventors have investigated for obtaining novel squarylium compounds having excellent photoconductive characteristics, in particular, high sensitivity, as well as novel cyclobutenedione derivatives which are used as intermediates for producing the squarylium compounds. As the result thereof, it has been discovered that the novel squarylium compounds described hereinafter are useful as a charge generating agent for electrophotographic light-sensitive materials and that novel cyclobutenedione derivatives are obtained by using specific tertiary aromatic amines, and the inventors have accomplished the present invention based on the discovery.

SUMMARY OF THE INVENTION

Thus, an object of this invention is to provide an electrophotographic light-sensitive material having high sensitivity using an organic photoconductor.

Another object of this invention is to provide a novel squarylium compound useful as a charge generating agent for electrophotographic light-sensitive materials and also a process of producing the squarylium compound.

A further object of this invention is to provide a novel cyclobutenedione derivative which is used as a raw material for producing the aforesaid squarylium compound.

That is, according to one embodiment of this invention, there is provided an electrophotographic light-sensitive material comprising a conductive support having formed thereon a light-sensitive layer containing a squarylium compound represented by formula (I) or (II):

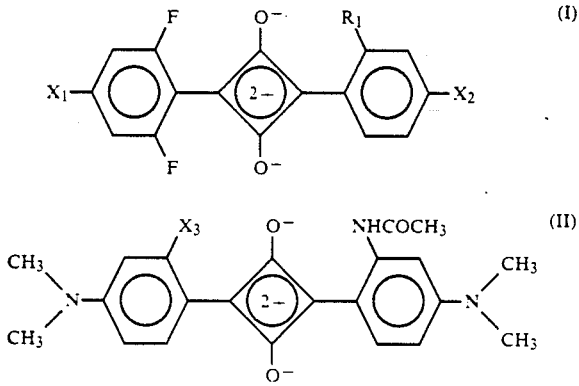

wherein $R_1$ represents a hydrogen atom, a methyl group, a carboxy group, a halogen atom (F, Cl, Br, and I), a trifluoromethyl group, an alkyl(preferably having from 1 to 10 carbon atoms)-substituted or phenyl-substituted carbonamido group, or an alkyl(preferably having from 1 to 10 carbon atoms)-substituted or phenyl-substituted sulfonamido group, $X_1$ and $X_2$, which may be the same or different, each represents a group shown by

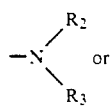

a group shown by

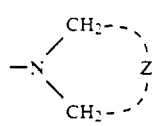

(wherein Z represents an atomic group necessary for forming a ring and $R_2$ and $R_3$, which may be the same or different, each represents an alkyl group having from 1 to 20 carbon atoms (preferably from 1 to 10 carbon atoms), a phenyl group, an unsubstituted benzyl group, or a benzyl group substituted with at least one of an alkyl group having from 1 to 6 carbon atoms, a hydroxy group, an alkoxy group having from 1 to 4 carbon atoms, a halogen atom (F, Cl, Br and I), a nitro group, a cyano group, an alkoxycarbonyl group having from 2 to 5 carbon atoms, and a trifluoromethyl group), and $X_3$ represents a hydrogen atom, a methyl group, a fluorine atom, or a hydroxy group.

A preferred embodiment of the squarylium compound shown by formula (I) described above is a squarylium compound shown by formula (III)

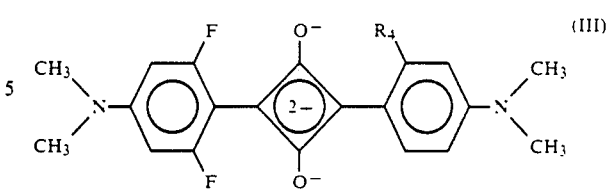

wherein $R_4$ represents a hydrogen atom, a methyl group, a fluorine atom, or a hydroxy group.

According to a further embodiment of this invention, there is provided the squarylium compound represented by formula (III) described above and a process of producing the compound of formula (III) as described hereinafter.

According to a still further embodiment of this invention, there is provided the squarylium compound represented by formula (II) described above and a process of producing the compound of formula (II) as described hereinafter.

According to another embodiment of this invention, there is provided a novel cyclobutenedione derivative presented by formula (IV);

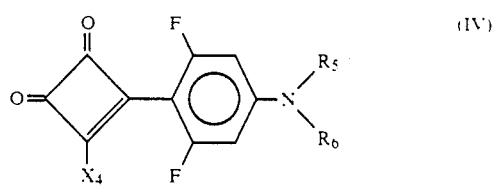

wherein $R_5$ and $R_6$ each represents a methyl group, an ethyl group, a propyl group, or a butyl group and $X_4$ represents a chlorine atom or a hydroxy group, said cyclobutenedione derivative being used as a raw material for producing the aforesaid squarylium compound of the type shown by formula (I) or (III).

According to another embodiment of this invention, there is also provided a novel cyclobutenedione derivative represented by formula (V)

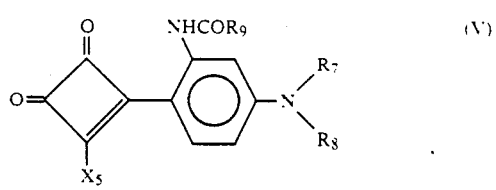

wherein $R_7$, $R_8$, and $R_9$ each represents a methyl group, an ethyl group, a propyl group, or a butyl group and $X_5$ represents a chlorine atom or a hydroxy group, said cyclobutenedione derivative being used as a raw material for producing the aforesaid squarylium compound of the type shown by formula (II).

According to another embodiment of this invention, there is further provided a novel cyclobutenedione derivative represented by formula (VI)

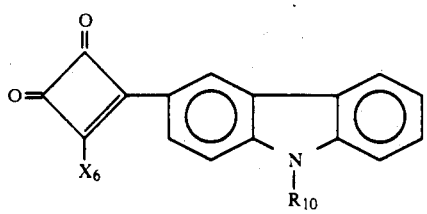

(VI)

wherein $R_{10}$ represents a methyl group, an ethyl group, a propyl group, or a butyl group and $X_6$ represents a chlorine atom or a hydroxy group, said cyclobutenedione derivative being used as a raw material for producing the aforesaid squarylium compound.

DETAILED DESCRIPTION OF THE INVENTION

Figure 1:
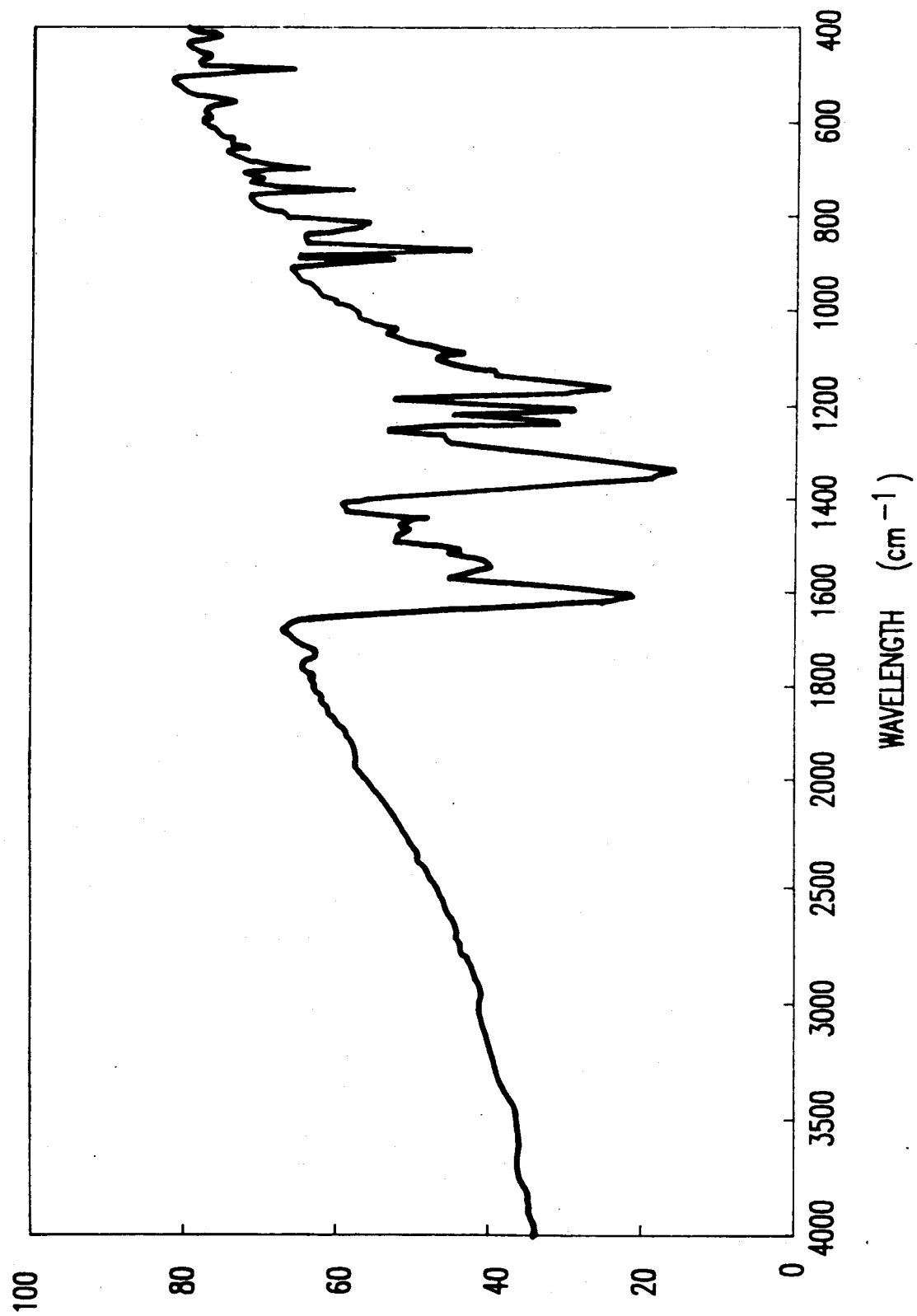
FIG. 1 is a graph showing the infrared absorption spectrum of the squarylium compound obtained in Example 6.

The squarylium compound shown by formula (I) described above, which is used for the electrophotographic, light-sensitive material, typically includes the squarylium compound shown by formula (III) described above.

Specific examples of the squarylium compound shown by formula (I), which can be used in this invention, including the squarylium compound of formula (III) are illustrated below.

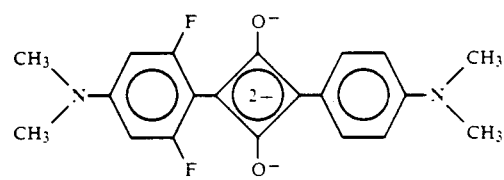

1

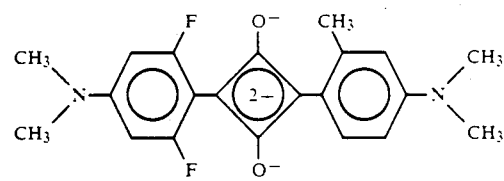

2

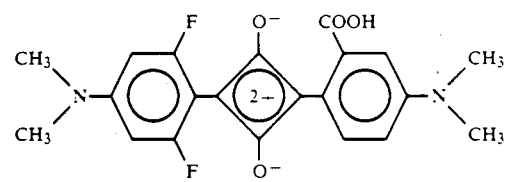

3

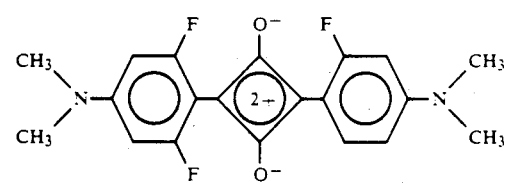

4

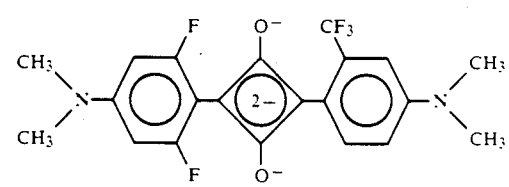

5

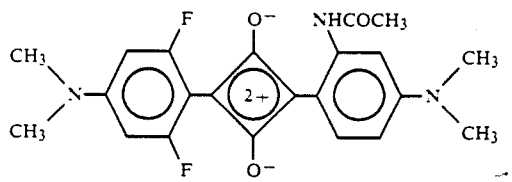
6
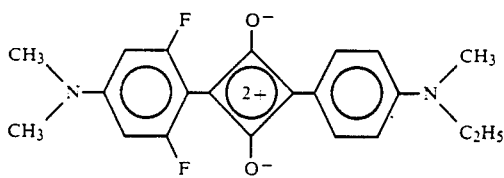
7
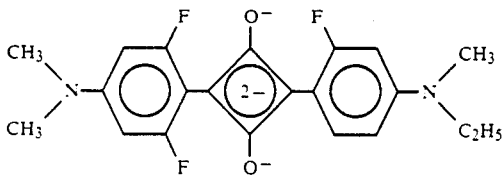
8
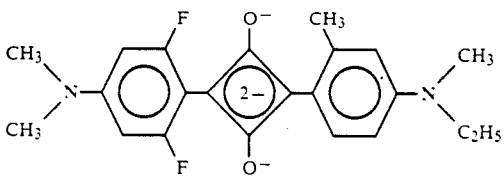
9
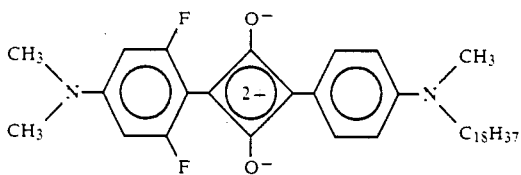
10
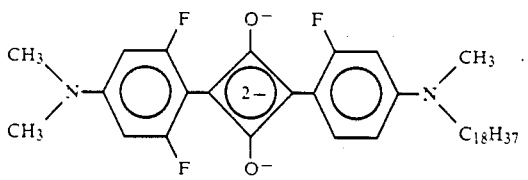
11
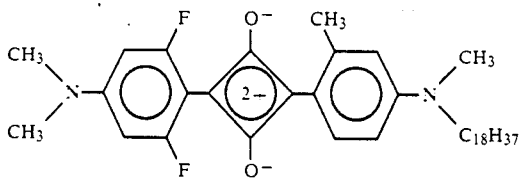
12
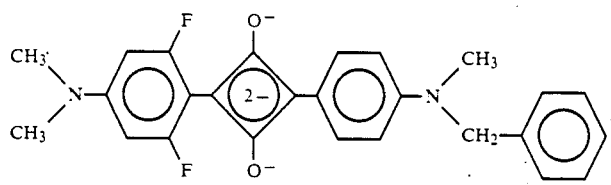
13
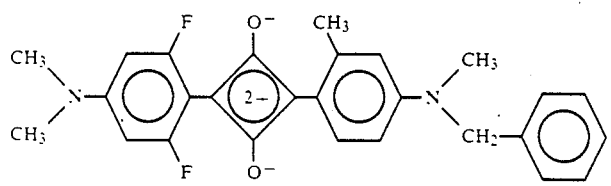
14

15
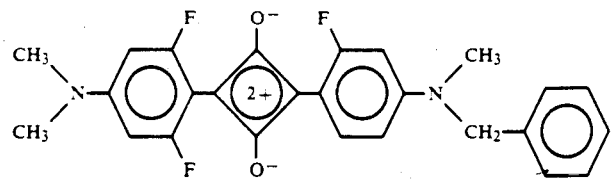
16
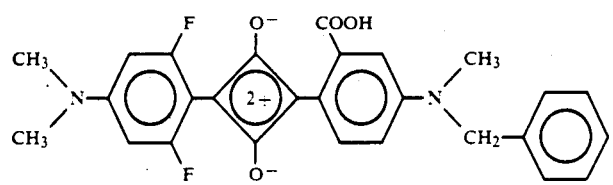
17
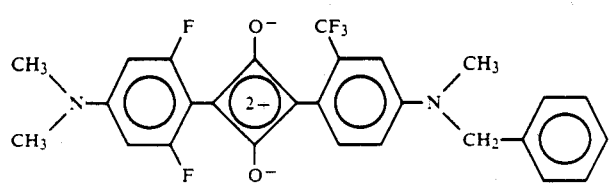
18
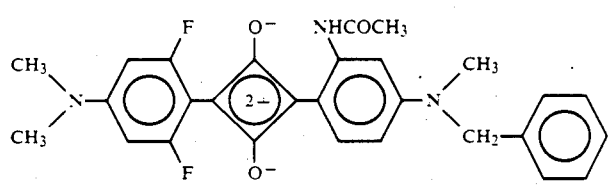
19
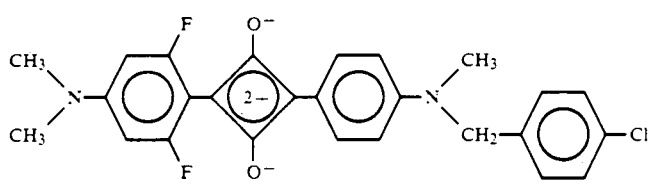
20
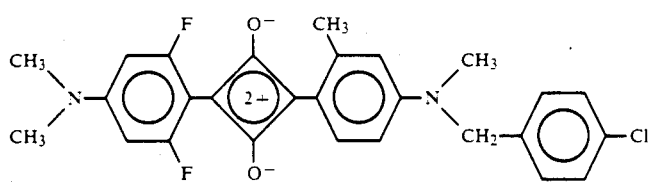
21
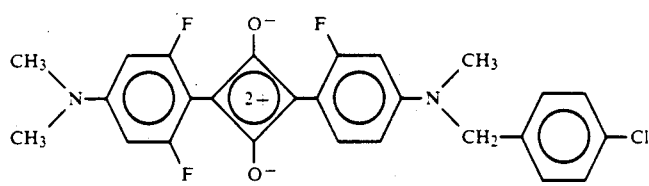
22
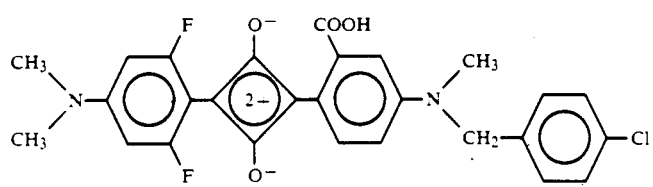
23
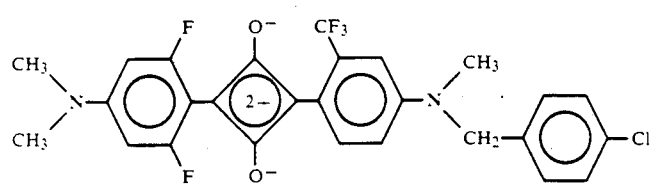

-continued
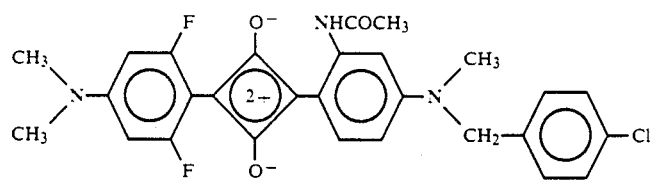
24
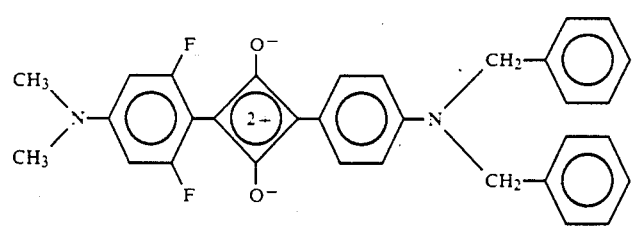
25
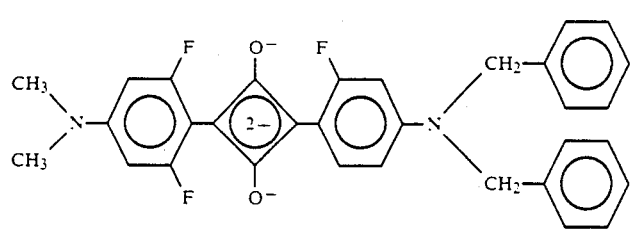
26
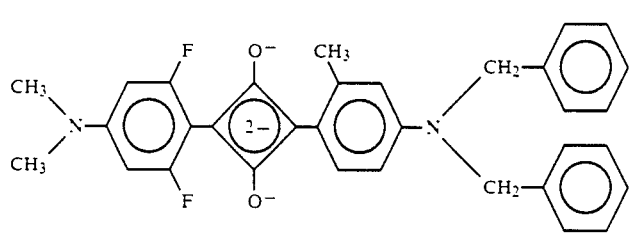
27
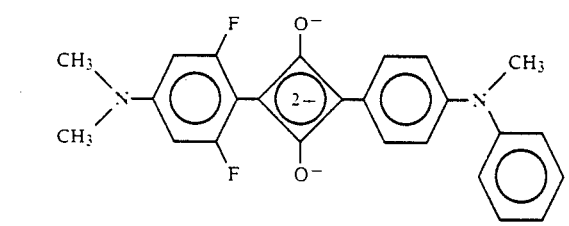
28
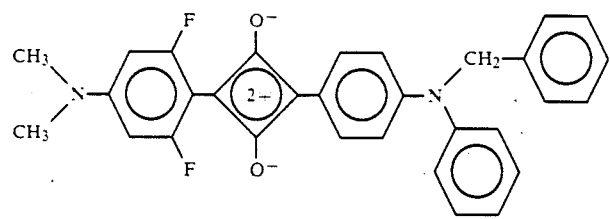
29
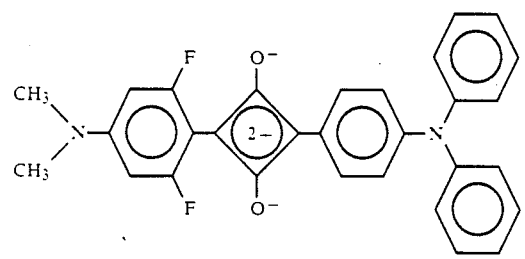
30

-continued
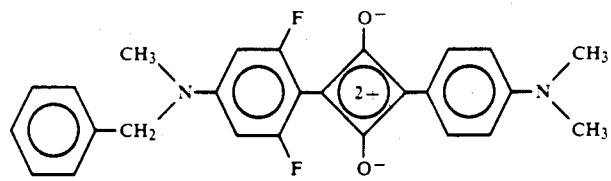
31
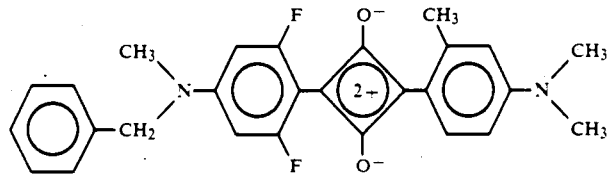
32
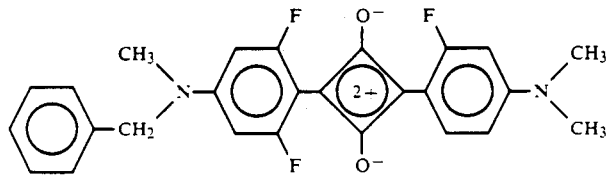
33
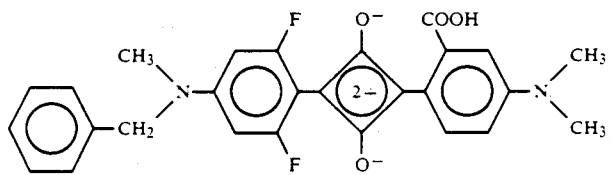
34
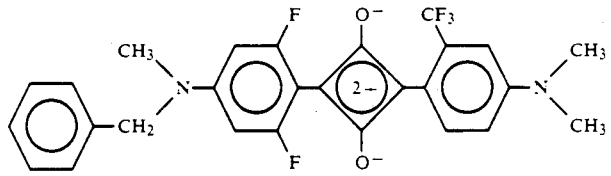
35
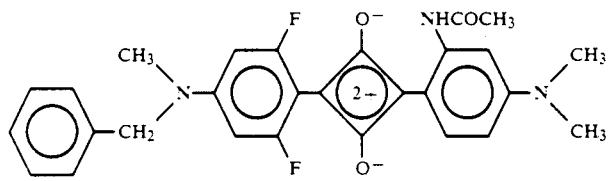
36
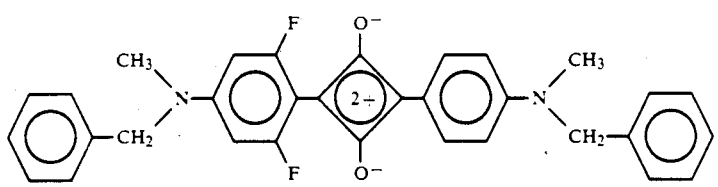
37
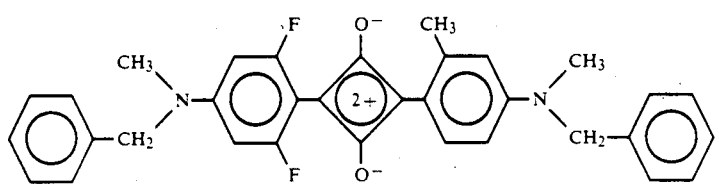
38
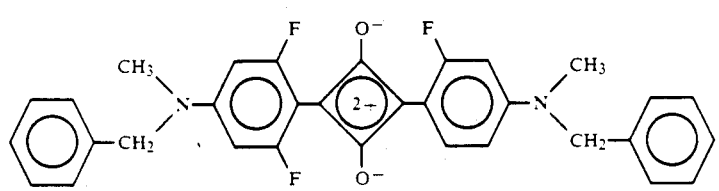
39

-continued
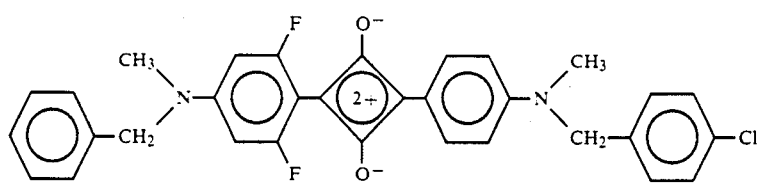
40
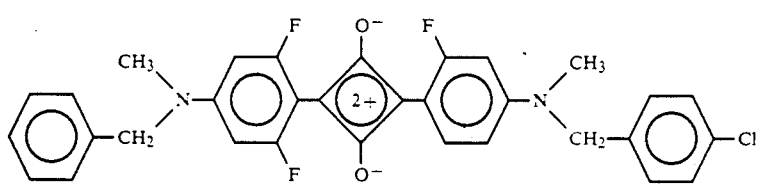
41
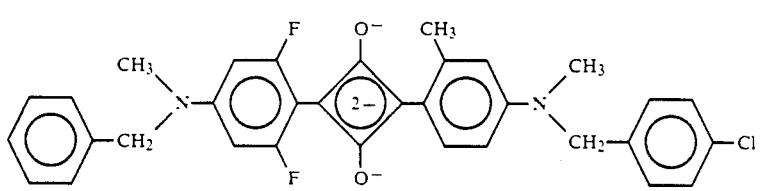
42
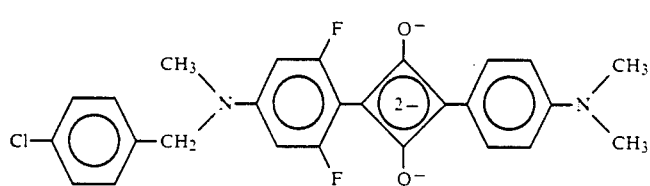
43
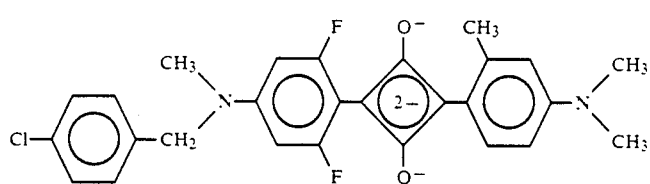
44
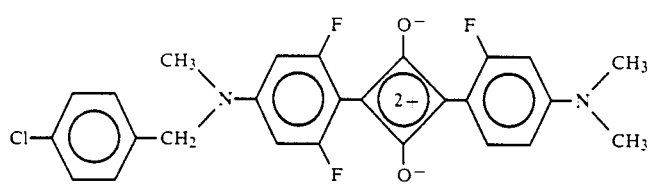
45
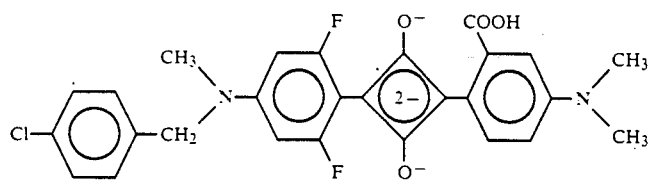
46
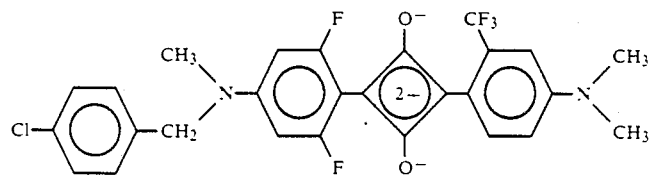
47

-continued
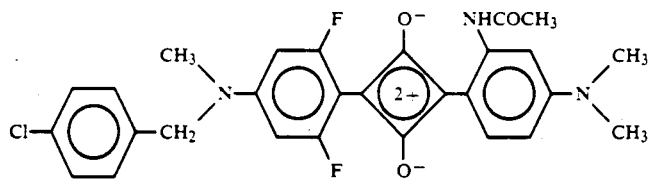
48
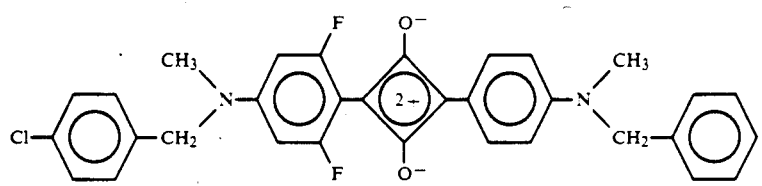
49
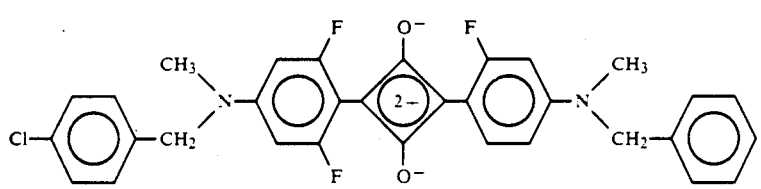
50
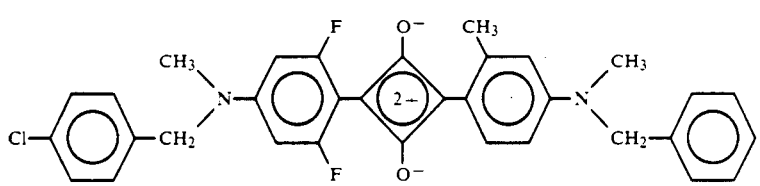
51
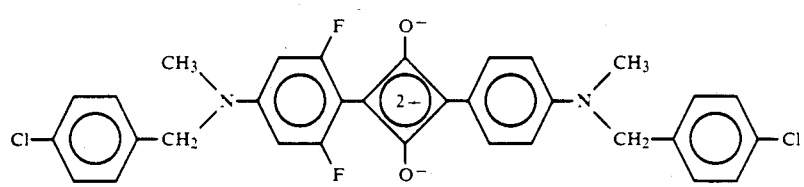
52
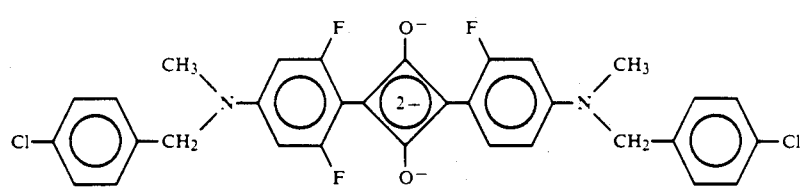
53
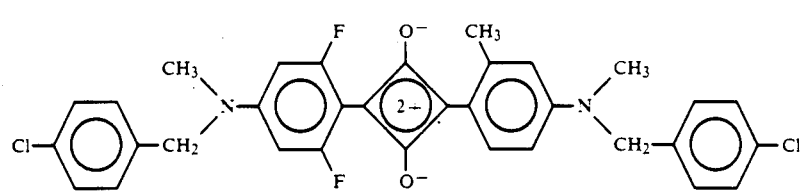
54
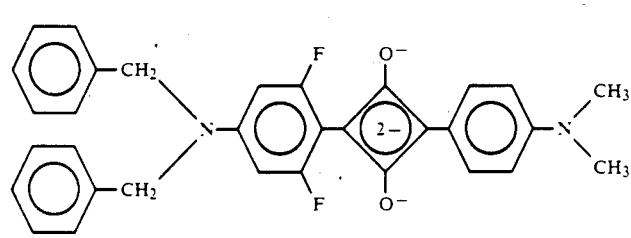
55

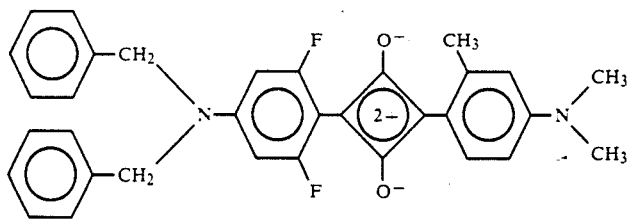
56
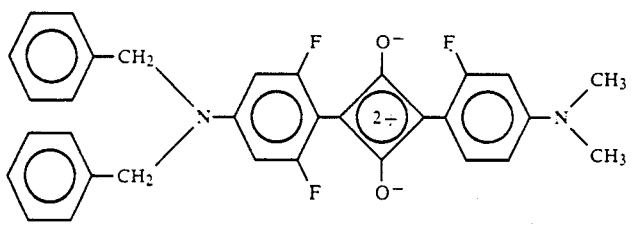
57
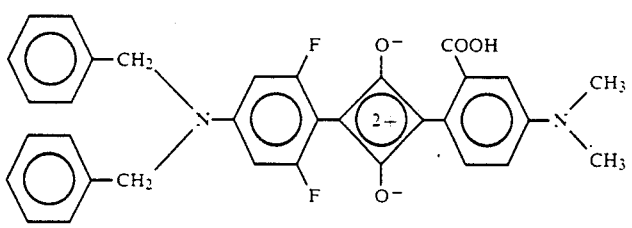
58
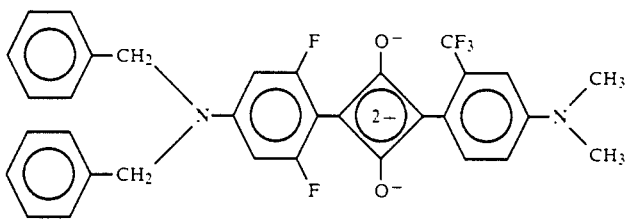
59
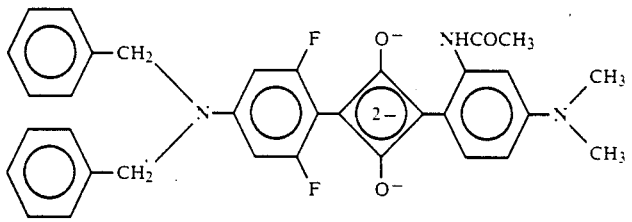
60
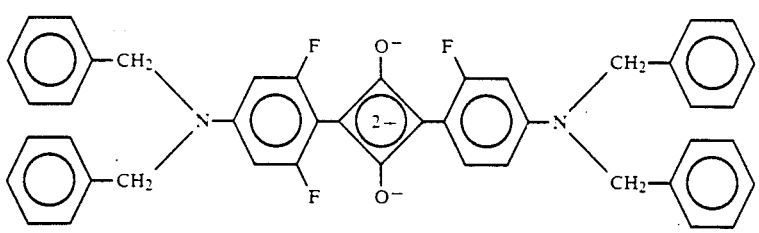
61
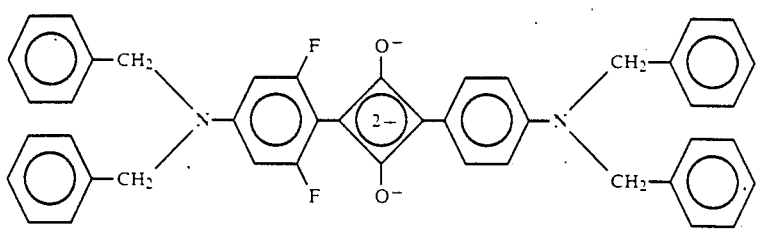
62

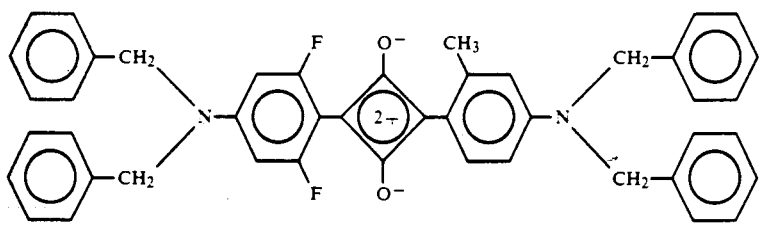

63

The squarylium compound shown by formula (I) described above is generally produced as follows.

That is, the compound can be produce by reacting 3,4-dichloro-3-cyclobutene-1,2-dione and a compound shown by formula (VII)

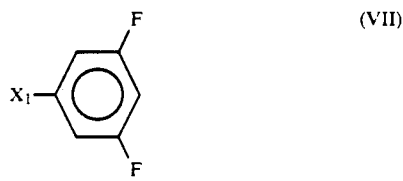

(VII)

(wherein $X_1$ has the same significance as defined above on formula (I)) in a proper solvent such as methylene chloride to provide a chlorocyclobutenedione derivative shown by formula (VIII)

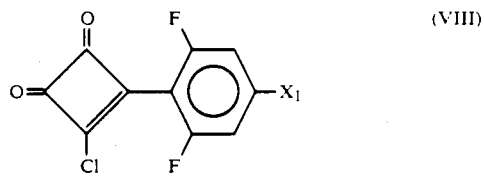

(VIII)

(wherein $X_1$ is the same as above), hydrolyzing the chlorocyclobutenedione derivative to provide a hydroxycyclobutenedione derivative shown by formula (IX)

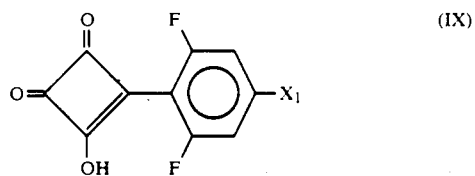

(IX)

(wherein $X_1$ is same as above), and reacting the hydroxycyclobutenedione and a compound shown by formula (X)

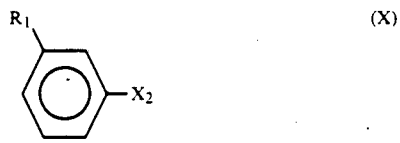

(X)

(wherein $R_1$ and $X_2$ have the same significance as defined above on formula (I)) by heating them in a proper solvent such as an aliphatic alcohol having from 4 to 8 carbon atoms (e.g., n-butyl alcohol and n-heptyl alcohol) or a mixture of the aforesaid aliphatic alcohol and an aromatic hydrocarbon (e.g., benzene and toluene).

In this invention, the aforesaid squarylium compound is incorporated in the light-sensitive layer formed on a conductive support. In this case, the electrophotographic light-sensitive material of this invention is generally classified into (1) an electrophotographic light-sensitive material comprising a conductive support having formed thereon a light-sensitive layer wherein the squarylium compound is dispersed in a binder resin containing a charge transporting material, (2) an electrophotographic light-sensitive material comprising a conductive support having formed thereon a light-sensitive layer wherein the squarylium compound and a charge transferring complex are dispersed in a binder resin, and (3) an electrophotographic light-sensitive material comprising a conductive support having formed thereon a charge generating layer having the squarylium compound dispersed in a binder resin and a charge transporting layer containing a charge transporting material.

The light-sensitive layer formed on a conductive support generally has a thickness of from 2 to 100 μm and preferably from 5 to 50 μm. In the case (3), the charge generating layer generally has a thickness of from 0.1 to 10 μm, preferably from 0.2 to 5 μm, and the charge transporting material generally has a thickness of from 5 to 50 μm, preferably from 10 to 30 μm.

As the conductive support in the electrophotographic light-sensitive material of this invention, there are plates of a metal such as aluminum, nickel, chromium, stainless steel, etc., metal drums, plastic films having formed thereon a metal foil or a thin layer of a metal or other conductive material, papers or plastic films coated or impregnated with a conductivity imparting agent, etc.

In this invention, in the case of dispersing the aforesaid squarylium compound in a binder resin of the light-sensitive layer formed on a conductive support, it is preferred that the squarylium compound is dispersed as fine particles thereof having particle sizes of less than 3 μm, preferably less than 0.3 μm and the amount thereof is preferably from 20 to 90% by weight, more preferably from 30 to 80% by weight, based on the total weight of binder resin and charge transporting material in the light-sensitive layer in the case (1), based on the weight of the light-sensitive layer in the case (2) and based o the weight of binder resin in the charge generating layer in the case (3), respectively.

As the binder resin for use in this invention, there are polystyrene, silicon resins, polycarbonate, acryl resins, methacryl resins, polyester, vinylic polymers (e.g., polyvinylbutyral), celluloses (e.g., cellulose esters and cellulose ethers), alkyd resins, etc., with polyester being preferred because of good adhesiveness to the support.

Also, as a charge transporting material which is used for the electrophotographic light-sensitive material of this invention, there are, for example, hydrazones such as N-methyl-N-phenylhydrazino-3-methylidene 9-ethylcarbazole, N,N-diphenylhydrazino-3-methylidene-9-ethylcarbazole, N,N-diphenylhydrazino-3-methylidene-9-methylcarbazole, p-diethylaminobenzaldehydo-N,N-diphenylhydrazone, p-diethylaminobenzaldehydo-N,N-di(p-methoxyphenyl)hydrazone, p-diethylnobenzaldehydo-N-(α-naphthyl)-N-phenylhydrazone, β,β-di(4-methoxyphenyl)acroleindiphenylhydrazone, etc.; pyrazolines such as 1-phenyl-3-(p-diethylaminostyryl) -5-(p-diethylaminostyryl)-5-(p-diethylaminophenyl)pyrazoline, 1-[quinolyl(2)]-3-(p-diethylaminostyryl) -5-(pdiethylaminophenyl)pyrazolidone, etc.; oxazole series compounds such as 2-(p-dipropylaminophenyl) -4-(p-dimethylaminophenyl)-5-(2-chlorophenyl)oxazole, 2-(p-diethylaminostyryl)-6-diethylaminobenzoxazole, etc.; oxadiazole series compounds such as 2,5-bis(p-diethylaminophenyl)-1,3,4-oxadiazole, 2,5-bis(4'-diethylamino-2'-methylphenyl) -1,3,4-oxadiazole, etc.; triarylmethane series compounds such as bis(4-diethylamino-2-methylphenyl) phenylmethane, etc.; triarylamine series compounds such as triphenylamine, 2,4',4''-trimethyltriphenylamine, 1,1-bis[4'-N,N-di(p-methylphenyl)aminophenyl]-cyclohexane, etc.; anthracene series compounds such as 5-(p-diethylaminostyrylanthracene, etc.; stilbene series compounds such as α-phenyl-4'-N,N-diphenylaminostilbene, 4'-N,N-di(p-methoxyphenyl)aminostilbene, etc.; and benzidine series compounds such as N,N'-diphenyl-N,N'-bis(3-methylphenyl) -[1,1'-biphenyl]-4,4'-diamine, 3,3'-dimethyl-N,N,N',N'-tetrakis (4-methylphenyl)-[1,1'-biphenyl]-4,4'-diamine, etc. Of these, hydrazones, triarylmethane series compounds, and benzidine series compounds are preferred. These materials are incorporated in a binder resin at use, and the weight ratio of the charge transporting material to the binder resin is preferably from 2/8 to 8/2 and more preferably from 3/7 to 7/3.

Furthermore, as other charge transporting materials, there are photoconductive polymers such as poly-N-vinylcarbazole, halogenated poly-N-vinylcarbazole, polyvinylanthracene, poly-9-vinylphenylanthracene, polyvinylacridine, polyvinylacenaphthilene, polyglycidylcarbazole, pyrene-formaldehyde resins, ethylcarbazole-formaldehyde resins, etc. These polymers each may form a layer by itself, i.e., without a binder resin. In the case (3), the polymer is preferably added in an amount of from 20 to 100% by weight, more preferably from 30 to 100% by weight, based on the weight of the charge transporting layer.

When the electrophotographic light-sensitive material of this invention has a light-sensitive layer of a double layer structure, it is preferred that the sensitivity of the electrophotographic light-sensitive material is high and the residual potential is low. In this case, the charge generating layer may be formed by dispersing the squarylium compound in a binder resin as described above and further the layer of the squarylium compound may be formed by sublimation or vapor deposition. Also, the upper layer may be the charge generating layer or the charge transporting layer. When the charge generating layer is formed as the upper layer, the electrophotographic light-sensitive material can be used as a positive charging type and when the charge transporting layer is formed as the upper layer, the light-sensitive material can be used as a negative charging type.

In the electrophotographic light-sensitive material, an adhesive layer may be formed between the aforesaid light-sensitive layer and the conductive support. The adhesive layer is composed of an ordinary synthetic resin, such as polyester, etc., and is usually formed as a thickness of from about 0.5 to 5 μm.

Then the squarylium compound shown by formula (III), which is a typical compound shown by formula (I) described is explained.

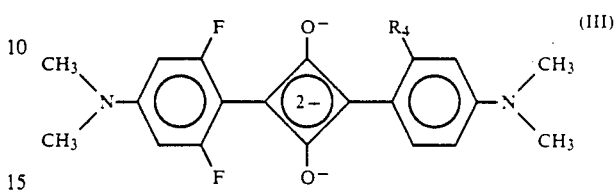

The squarylium compound shown by formula (III) can be produced by reacting 3,4-dichloro-3-cyclobutene-1,2-dione shown by formula (III-1)

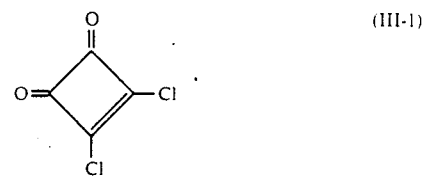

and 3,5-difluoro-N,N-dimethylaniline shown by formula (III-2)

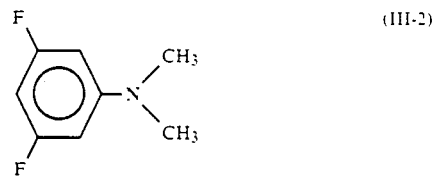

to provide a chlorocyclobutenedione derivative shown by formula (III-3)

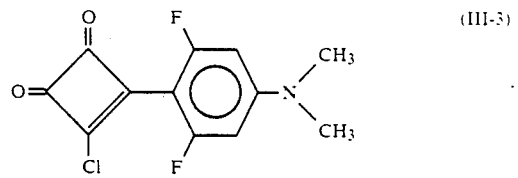

then, hydroxyzing the chlorocyclobutenedione derivative to provide a hydroxycyclobutenedione derivative shown by formula (III-4)

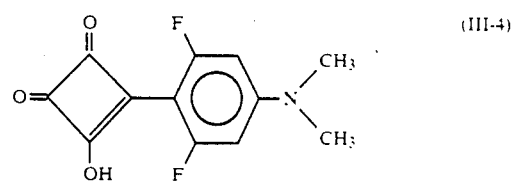

and reacting the hydrocyclobutenedione derivative and an aniline derivative shown by formula (III-5)

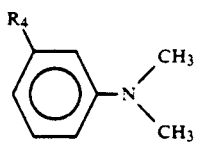

wherein R₄ is the same as defined above with respect to formula (III).

In the aforesaid production process, the reaction in each step can be practiced according to a similar known reaction.

That is, 3,4-dichloro-3-cyclobutene-1,2-dione is first reacted with 3,5-difluoro-N,N-dimethylaniline shown by formula (III-2) described above and the reaction can be performed by dissolving these components in a proper solvent such as a halogenated hydrocarbon (e.g., methylene chloride, carbon tetrachloride, and chloroform) or an ordinary Friedel-Craft reaction solvent (e.g., nitrobenzene, ethyl ether, and acetonitrile) and stirring the solution at temperature from 0° to 40° C., preferably from 25° to 40° C., in the existence, if desired, of a catalyst such as boron trifluoride ethyl ether complex, aluminum chloride, antimony chloride, iron(II) or (III) chloride, titanium(IV) chloride, tin(IV) chloride, bithmus(IV) chloride, zinc(II) chloride, mercury chloride, etc., preferably aluminum chloride and boron trifluoride ethyl ether complex. The catalyst is generally used in an amount more than equivalent to 3,4-dichloro-3-cyclobutene-1,2-dione.

The chlorocyclobutenedione derivative thus obtained is then hydrolyzed and the hydrolysis is performed by heating the derivative in water containing a proper acid, such as acetic acid, hydrochloric acid and sulfuric acid, at about 100° C. to thereby obtain the hydroxycyclobutenedione derivative shown by formula (III-4).

Then, the hydroxycyclobutenedione derivative obtained by the hydrolysis is reacted with the aniline derivative shown by aforesaid formula (III-5). Examples of the aniline derivative include N,N-dimethylaniline, 3-methyl-N,N-dimethylaniline, 3-fluoro-N,N-dimethylaniline, and 3-hydroxy-N,N-dimethylaniline. The reaction can be performed by heating these compounds at a temperature of from 90° to 160° C., preferably from 90° to 100° C., in a proper solvent such as an aliphatic alcohol having from 4 to 8 carbon atoms (e.g., n-butyl alcohol and n-heptyl alcohol) or a mixture of the aliphatic alcohol and an aromatic hydrocarbon (e.g., benzene and toluene).

Then, the squarylium compound shown by formula (II) is explained.

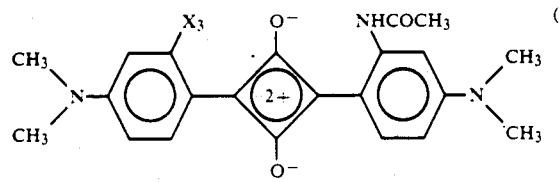

The squarylium compound of formula (II) is produced as follows.

In the 1st process, the squarylium compound can be obtained by reacting 3,4-dichloro-3-cyclobutene-1,2-dione shown by formula (II-1)

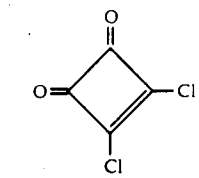

and an aniline derivative shown by formula (II-2)

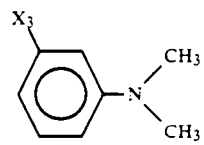

(wherein X₃ has the same significance as defined above on formula (II)) to provide a chlorocyclobutenedione derivative shown by formula (II-3)

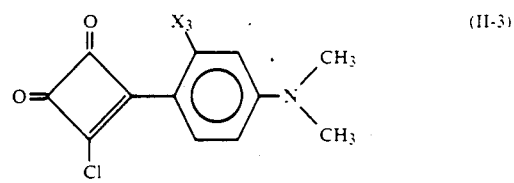

then, the hydroxyzing the chlorocyclobutenedione derivative thus obtained to provide a hydroxybutenedione derivative shown by formula (II-4)

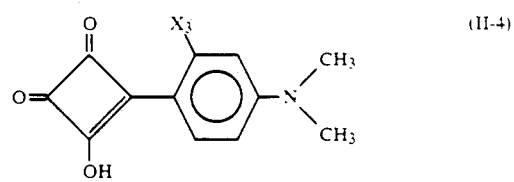

and further reacting the hydroxycyclobutenedione derivative and 3-acetylamino-N,N-dimethylaniline shown by formula (II-5)

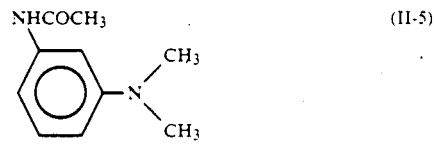

In the 2nd process, the squarylium compound of formula (II) can be obtained by reacting 3,4-dichloro-3-cyclobutene-1,2-dione shown by formula (II-1) described above and 3-acetylamino-N,N-dimethylaniline shown by formula (II-5) described above to provide a chlorocyclobutenedione derivative shown by formula (II-6)

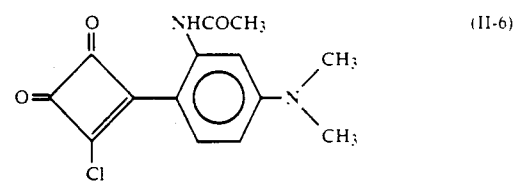

then, hydrolyzing the chlorocyclobutenedione derivative thus obtained to provide a hydroxycyclobutenedione derivative shown by formula (II-7)

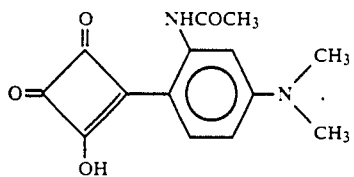
(II-7)

and reacting the hydroxychlorobutenedione derivative and the aniline derivative shown by formula (II-2) described above.

In the aforesaid production processes, the reaction in each step can be practiced according to a similar known reaction.

That is, first, 3,4-dichloro-3-cyclobutene-1,2-dione is reacted with the aniline derivative shown in formula (II-2) in the 1st process or with 3-acetylamino-N,N-dimethylaniline shown by formula (II-5) in the 2nd process, followed by hydrolysis. The aniline derivative shown by formula (II-2) is exemplified with those described with respect to formula (III-5) above. The aforesaid reactions can be performed using the components in the same manner as in the reactions for production of the hydroxycyclobutenedione derivative shown by formula (III-4).

Then, the hydroxycyclobutenedione derivative obtained by the hydrolysis is reacted with 3-acetylamino-N,N-dimethylaniline shown by formula (II-5) in the 1st process or with the aniline derivative shown by formula (II-2) in the 2nd process and the reaction can be performed by heating these components in a solvent in the same manner as in the reaction of the compound of formulae (III-4) and (III-5) described above.

The squarylium compounds of formula (II) and (III) as produced above are useful as a charge generating agent for an electrophotographic light-sensitive material. For example, when a light-sensitive layer of an electrophotographic light-sensitive material has a functionally separated double layer structure of a charge generating layer and a charge transporting layer, the charge generating layer can be formed using the aforesaid squarylium compound together with a film-forming resin.

Then, novel cyclobutenedione derivatives which are used as the raw materials for producing the aforesaid squarylium compounds of this invention are explained.

The cyclobutenedione derivatives shown by formulae (IV) and (V) of this invention, which are used as a raw material for the squarylium compound of this invention described above are explained.

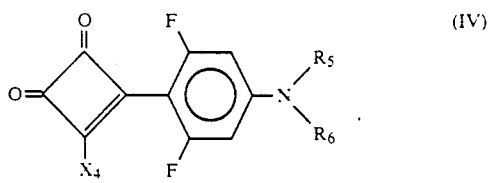
(IV)

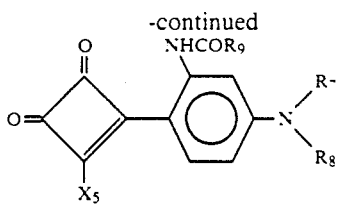
(V)

In formula (IV) and (V), $X_4$, $X_5$, $R_5$, $R_6$, $R_7$, $R_8$ and $R_9$ are defined above, and $R_5$, $R_6$ and $R_9$ are preferably a methyl group.

The cyclobutenedione derivatives shown by formula (IV) and (V) can be produced by reacting 3,4-dichloro-3-cyclobutene-1,2-dione and an aniline derivative shown by formula (IV-1) or (V-1)

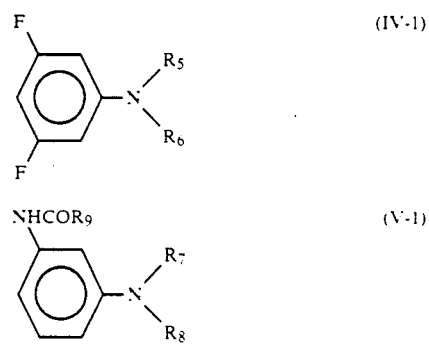

(wherein $R_5$, $R_6$, $R_7$, $R_8$ and $R_9$ are the same as above) to provide a chlorocyclobutenedione derivative, and, if desired, hydrolyzing the chlorocyclobutenedione derivative.

The aforesaid reactions can be practiced in the same manner as in the production of the compounds of formula (III-3) or (III-4), and formula (II-6) or (II-7), respectively.

Examples of the 3,5-difluoroaniline derivative of formula (IV 1) include 3,5-difluoro-N,N-dimethylaniline, 3,5-difluoro-N,N-diethylaniline, 3,5-difluoro-N,N-dipropylaniline and 3,5-difluoro-N,N-dibutylaniline.

The cyclobutenedione derivative shown by formula (VI) which can be also used as a raw material for producing squarylium compounds is explained.

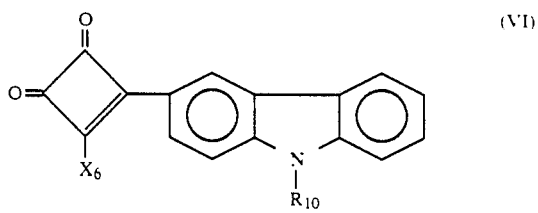
(VI)

The cyclobutenedione derivative of formula (VI) can be produced by reacting 3,4-dichloro-3 cyclobutene-1,2-dione and a carbazole derivative shown by formula (VI-1)

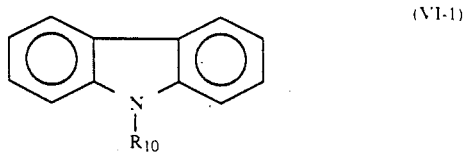
(VI-1)

(wherein $R_{10}$ is the same as above) to provide a chlorocyclobutenedione derivative, and, if desired, hydrolyzing the chlorocyclobutenedione derivative thus obtained. The reactions can be practiced in the same manner as in the production of the cyclobutenedione derivative shown by formulae (IV) and (V).

Examples of the carbazole derivative of formula (VI-1) include N-methylcarbazole, N-ethylcarbazole, N-propylcarbazole, and N-butylcarbazole.

The cyclobutenedine derivatives of formulae (IV), (V) and (VI) are useful as a raw material of squarylium compounds which are useful for electrophotographic light-sensitive material as well as recording material for optical disc, solar batteries, infrared cut filters, etc.

For example, various squarylium compounds can be producing by condensing the cyclobutenedione derivatives of this invention with an aniline derivative shown by formula (VII)

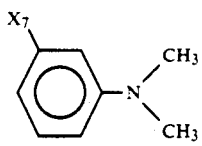
(VII)

wherein $X_7$ represents a hydrogen atom, a methyl group, a fluorine atom, or a hydroxy group.

Then, the invention is further explained more practically by the following examples.

EXAMPLE 1

A mixture of 1 part by weight of Squarylium Compound 1 described hereinbefore, 1 part by weight of polyester resin ("Adhesive 49000", trade name, made by Du Pont) and 10 parts by weight of tetrahydrofuran was ground for 4 hours with a ball mill, and the dispersion thus formed was coated on a polyester film vapor-deposited with aluminum ("Metalmee", trade name, made by Toray Inductires, Inc.) by a bar coater and dried for 5 hours at 70° C. to form a charge generating layer of 1 μm thick.

On the charge generating layer was coated a homogeneous solution composed of 1 part by weight of N,N'-diphenyl-N,N'-bis(3-methylphenyl) -[1,1'-biphenyl]-4,4'-diamine, 1 part by weight of a polycarbonate resin ("Panlite", trade name, made by Teijin Limited) and 10 parts by weight of tetrahydrofuran using an applicator and dried for 5 hours at 70° C. to form a charge transporting layer of 22 μm thick. Thus, an electrophotographic light-sensitive material was prepared.

Then, after negatively charging the light-sensitive material by applying corona dicharging of −6 KV, the light-sensitive material was allowed to stand in the dark for 2 seconds and the light-sensitive layer was irradiated by light using a tungsten lamp so that the illuminance at the surface became 10 lux. Then the exposure amount ($E_{\frac{1}{2}}$) to reduce the surface potential to $\frac{1}{2}$ of the surface potential ($V_{DDP}$) after allowing to stand in the dark was measured using an electrostatic copying paper test machine (Electrostatic Paper Analyzer SP-428, made by Kawaguchi Denki K.K.). The results were as follows.

Initial Charged Potential $V_0$: −1030 V
Potential ($V_{DDP}$) after allowing to stand in the dark for 2 seconds: −970 V
$E_{\frac{1}{2}}$: 2.0 lux. sec.
Residual Potential $R_P$: 0 V.

The following measurement was also performed. After applying corona discharging onto the aforesaid electrophotographic light-sensitive material in the dark, the electrophotographic light-sensitive material was irradiated by monochromatic light of 1 μw/cm² having wavelength of 800 nm using a monochromatic meter. Then, the time of reducing the surface potential to $\frac{1}{2}$ of the original potential ($V_{DDP}$) was measured and the exposure amount was determined. The exposure amount obtained was 9.9 ergs/cm². It is seen from the result that the electrophotographic light-sensitive material of this invention had very excellent sensitivity for light of long wavelength.

EXAMPLE 2

By following the same procedure as Example 1 except each of Squarylium Compounds 2, 4, 19 and 25 was used in place of Compound 1, electrophotographic light-sensitive materials were prepared and they were evaluated as in Example 1. The results are shown in Table 1.

TABLE 1

| Example No. | Squarylium Compound | $V_0$ (V) | $V_{DDP}$ (V) | $E_{1/2}$ (lux. sec.) | $R_P$ (V) | Half Decay Exposure at 800 nm (erg · cm²) |
|---|---|---|---|---|---|---|
| 2 | 2 | −910 | −880 | 3.2 | 0 | 16.7 |
| 3 | 4 | −980 | −930 | 1.3 | 0 | 6.9 |
| 4 | 19 | −1040 | −1000 | 1.9 | 0 | 9.6 |
| 5 | 25 | −890 | −870 | 2.9 | 0 | 15.1 |

From the results shown above, it can be seen that the electrophotographic light-sensitive material having the light-sensitive layer containing the squarylium compound shown by formula (I) has excellent charging property, low residual potential, and is excellent in sensitivity.

The following examples show the squarylium compound shown by formula (III).

EXAMPLE 6

In 15 ml of methylene chloride were dissolved 3.64 g (24.1 mmol) of 3,4-dichloro-3-cyclobutene-1,2-dione, 7.54 g (48.0 mmol) of 3,5-fifluoro-N,N-dimethylaniline, and 7.2 g (48.0 mmol) of a boron trifluoride ethyl ether complex and the solution was stirred for 24 hours at room temperature to perform reaction. After the reaction was over, the reaction mixture was washed with diluted hydrochloric acid and then with water, and separated and purified using column chromatography to provide 2.31 g (yield 35%) of the chlorocyclobutenedione derivative shown by formula (III-3) described above. Melting point: 189° to 190° C.

After adding 10 ml of acetic acid and 5 ml of water to 2.01 g (7.4 mmol) of the thus obtained chlorocyclobutenedione derivative and refluxing the solution for 2 hours, the reaction mixture was allowed to cool and precipitates thus deposited were collected by filtration to provide 1.61 g (yield 85%) of the hydroxycyclobutenedione derivative shown by formula described above.

ultraviolet absorption wavelengths (maximum) of these compounds are also shown in Table 2.

TABLE 2

| Example No. | Desired Compound | UV (CH$_2$Cl$_2$) (nm) |
|---|---|---|
| 7 | (CH$_3$)$_2$N-C$_6$H$_4$-[squarylium 2-]-C$_6$H$_3$F$_2$-N(CH$_3$)$_2$ | 620 |
| 8 | (CH$_3$)$_2$N-C$_6$H$_3$(CH$_3$)-[squarylium 2-]-C$_6$H$_3$F$_2$-N(CH$_3$)$_2$ | 625 |
| 9 | (CH$_3$)$_2$N-C$_6$H$_3$F-[squarylium 2-]-C$_6$H$_2$F$_2$-N(CH$_3$)$_2$ | 622 |

Then after stirring 1.50 g (5.92 mmol) of the hydroxycyclobutenedione derivative and 0.82 g (6.1 mmol) of 3 hydroxy-N,N-dimethylaniline in 60 ml of butanol for hours with heating at about 110° C., deposits formed were collected by filtration to provide blue-green crystals. By washing the crystals with methanol and then diethyl ether and drying, 1.98 g (yield 90%) of a squarylium compound shown by the following formula was obtained. Melting point: 302° C. (decomposed)

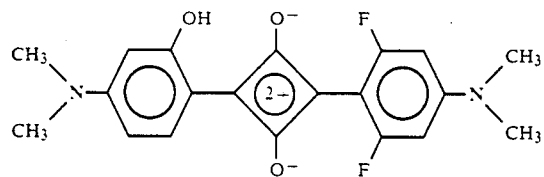

The infrared absorption spectra of the compound are shown in FIG. 1. The ultraviolet absorption spectra (maximum) UV (CH$_2$Cl$_2$) was at 614 nm.

Also, the element analysis thereof for C$_{20}$H$_{18}$F$_2$N$_2$O$_3$ was as follows.

|  | Calculated (%) | Found (%) |
|---|---|---|
| C | 64.51 | 64.54 |
| H | 4.87 | 4.97 |
| N | 7.52 | 7.50 |

EXAMPLES 7 to 9

By following the same procedure as in Example 6, the hydroxycyclobutenedione derivative shown by formula (III-4) was prepared and by reacting the product and each of N,N-dimethylaniline, 3-methyl-N,N-dimethylaniline, and 3-fluoro-N,N-dimethylaniline by the same manner as in Example 6, the squarylium compounds shown in Table 2 below were prepared. The Then, the following examples show the squarylium compounds shown by formula (II) described above.

EXAMPLE 10

In 60 ml of methylene chloride were dissolved 15.1 g (0.1 mol) of 3,4-dichloro-3-cyclobutene-1,2-dione, 60 ml (0.5 mmol) of N,N-dimethylaniline, and 13 ml (0.1 mol) of a boron trifluoride ethyl ether complex, and the solution was stirred for 5 hours at room temperature to perform reaction. After the reaction was over, the reaction mixture was washed with diluted hydrochloric acid and then with water, and separated and purified using column chromatography to provide 19.0 g (yield 81%) of the chlorocyclobutenedione compound shown by the following formula

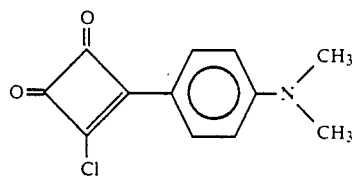

To 19.0 g (0.8 mol) of the chlorocyclobutenedione compound thus obtained were added 75 ml of acetic acid and 25 ml of water followed by refluxing for one hour. Then, the reaction mixture was allowed to cool and precipitates formed were collected by filtration to provide 17.2 g (yield 98%) of the hydroxycyclobutenedione compound shown by the following formula.

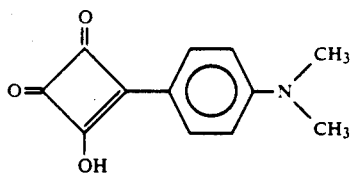

After stirring 1.00 g (4.60 mmol) of the hydroxycyclobutenedione compound and 1.64 g (9.20 mmol) of 3-acetylamino-N,N-dimethylaniline in 100 ml of butanol for 5 hours with heating at about 110° C., crystals deposited were collected by filtration and washed with methanol and then diethyl ether to provide 1.60 g (yield 92%) of the squarylium compound shown by the following formula. Melting point: 266° C. (decomposed)

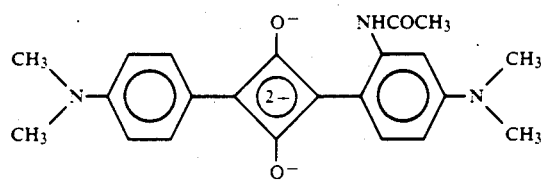

Figure 2:
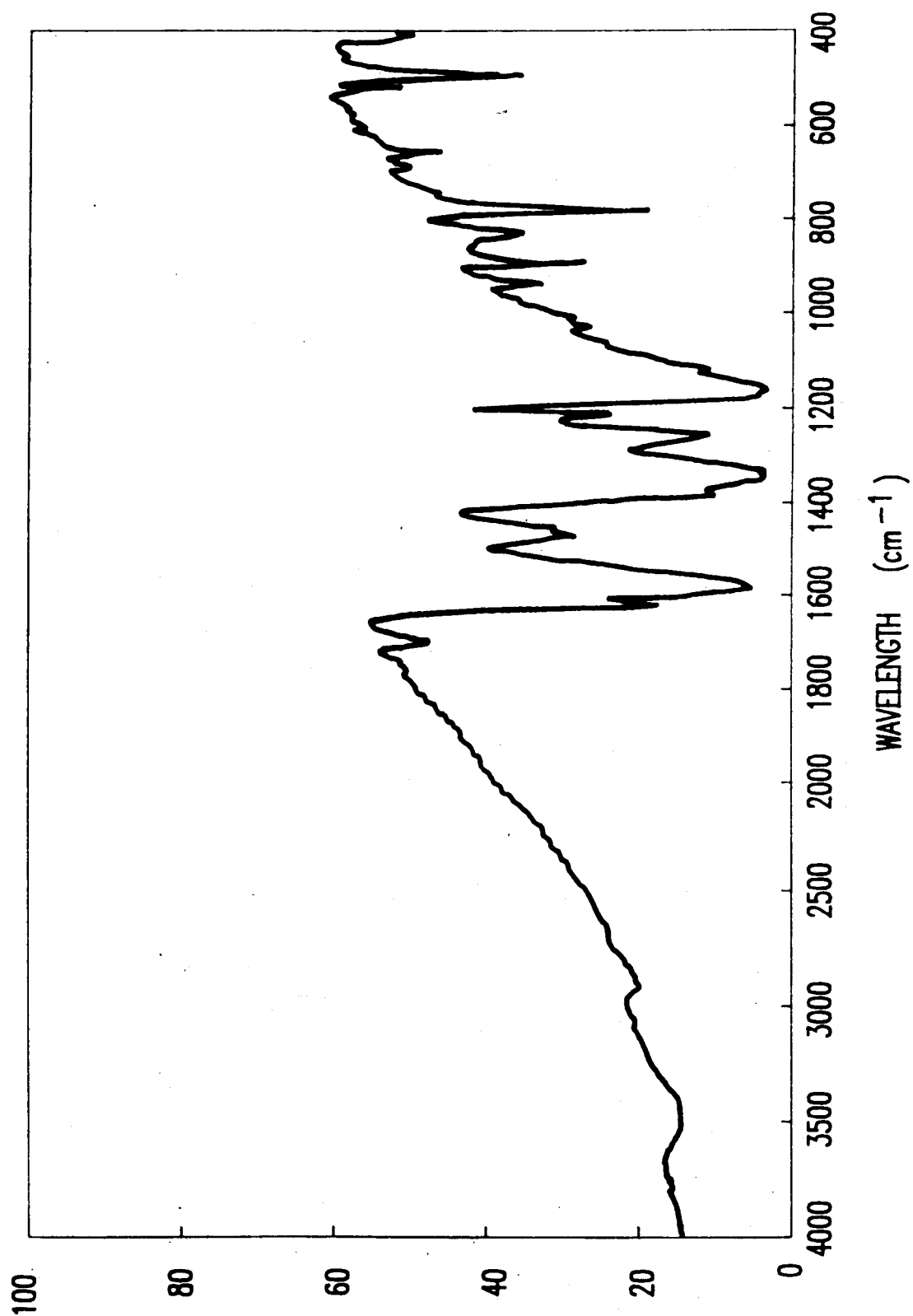
FIG. 2 is a graph showing the infrared absorption spectrum of the squarylium compound obtained in Example 10.

The infrared absorption spectra are shown in FIG. 2. The ultraviolet absorption wavelength (maximum) UV(CH$_2$Cl$_2$) was 648 nm. Also, the elemental analysis for C$_{22}$H$_{23}$N$_3$O$_3$ was as follows.

|   | Calculated (%) | Found (%) |
|---|---|---|
| C | 70.01 | 69.89 |
| H | 6.14 | 6.13 |
| N | 11.13 | 11.10 |

EXAMPLE 11

In 20 ml of methylene chloride were dissolved 1.93 g (12.8 mmol) of 3,4-dichloro-3-cyclobutene-1,2-dione and 4.52 g (25.4 mmol) of 3-acetylamino-N,N-dimethylaniline, and the solution was stirred for 2 hours at room temperature to perform reaction. After the reaction was over, the reaction mixture was washed with diluted hydrochloric acid and then with water, and separated and purified using column chromatography to provide 2.16 g (yield 58%) of the chlorocyclobutenedione compound shown by formula (II-6) described above. Melting point: 218° C. (decomposed)

After adding 10 ml of acetic acid and 1 ml of water to 1.00 g (3.42 mmol) of the chlorocyclobutenedione compound thus obtained and refluxing for 10 minutes, the reaction mixture obtained was allowed to cool and the precipitates deposited were collected by filtration to provide 0.86 g (yield 92%) of the hydroxycyclobutenedione compound shown (II-7) described above. Melting point: 280° C. (decomposed)

After stirring 0.55 g (2.0 mmol) of the hydrocyclobutenedione and 0.30 g (2.2 mmol) of hydroxy-N,N-dimethylaniline in 20 ml of butanol for 5 hours under heating at about 110° C., crystals deposited were collected by fi and washed with methanol and then with diethy to provide 0.75 g (yield 95%) of a squarylium shown by the following formula. Melting point 303° C. (decomposed).

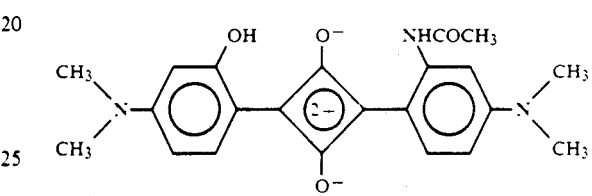

Figure 3:
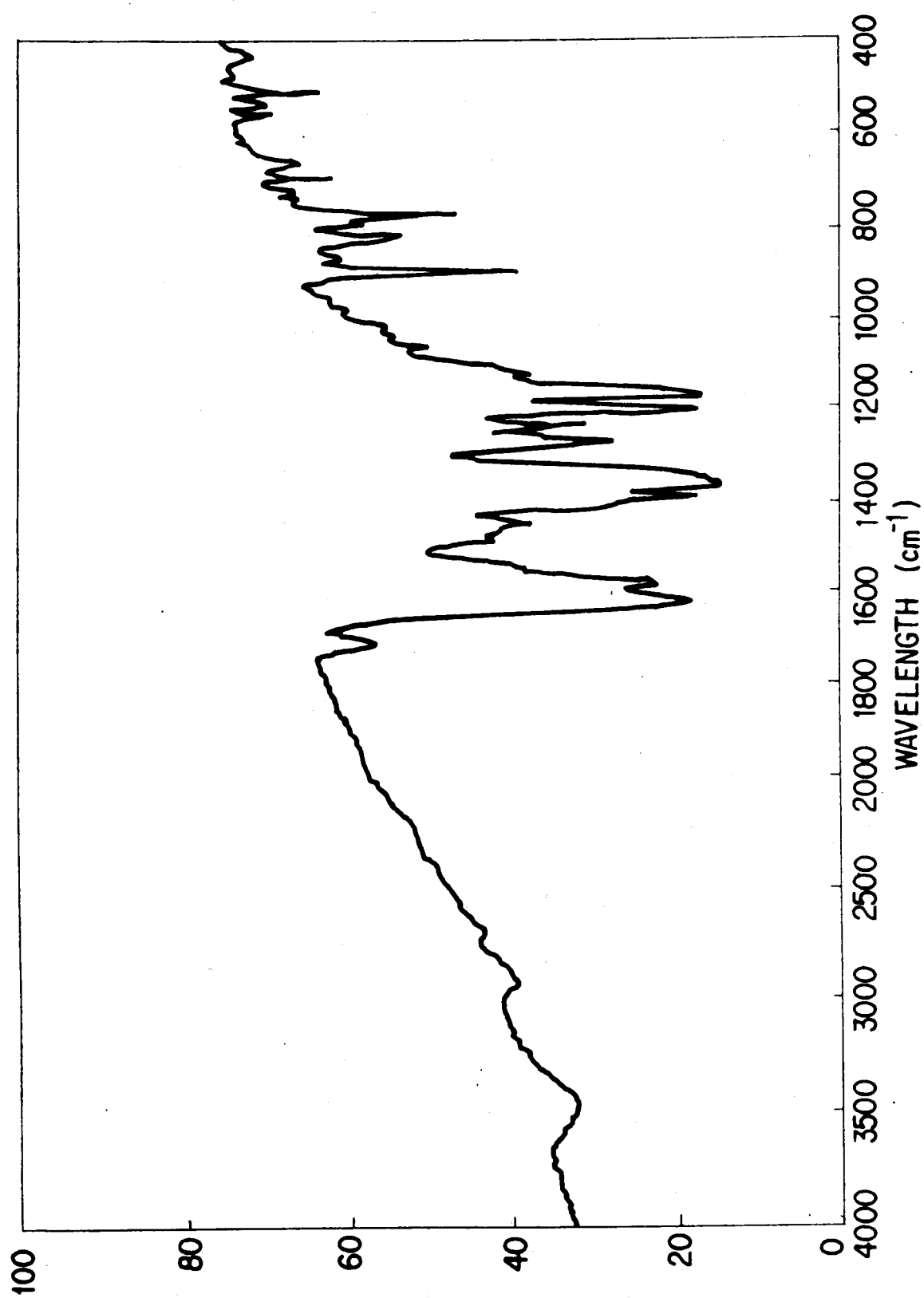
FIG. 3 is a graph showing the infrared absorption spectrum of the squarylium compound obtained in Example 11.

The infrared absorption spectra of the compound are shown in FIG. 3.

The ultraviolet absorption wavelength (maximum) UV(CH$_2$Cl$_2$) was 653 nm. the elemental analysis of the compound for C$_{22}$H$_{23}$N$_2$O$_4$ is as follows.

|   | Calculated (%) | Found (%) |
|---|---|---|
| C | 67.16 | 67.14 |
| H | 5.89 | 5.92 |
| N | 10.68 | 10.73 |

EXAMPLES 12 and 13

By following the same procedure as Example 10 but changing the raw materials, the hydroxycyclobutenedione derivatives shown in Table 3 below were prepared and by the same manner as in Example 10, the squarylium compounds shown in Table 3 were prepared. The ultraviolet absorption wavelength (maximum) of each of the compounds is shown in Table 3.

TABLE 3

| Sample No. | Hydroxycyclobutenedione derivative | Squarylium Compound | UV (CH$_2$Cl$_2$) |
|---|---|---|---|
| 12 | (structure) | (structure) | 646 nm |
| 13 | (structure) | (structure) | 656 nm |

Then, the following examples show the cyclobutenedione derivative shown by formula (IV) described above.

EXAMPLE 14

In 15 ml of methylene chloride were dissolved 3.64 g (24.1 mmol) of 3,4-dichloro-3-cyclobutene-1,2-dione, 7.54 g of (48.0 mmol) of 3,5-difluoro-N,N-dimethylaniline, and 7.2 g (48.0 mmol) of a boron trifluoride ethyl ether complex, and the solution was stirred for 24 hours at room temperature to perform reaction. After the reaction was over, the reaction mixture was washed with diluted hydrochloric acid and then with water, and separated and purified using column chromatography to provide the chlorocyclobutene compound of 2.31 g (yield 35%) shown by the following formula. Melting point: 189 to 190° C.

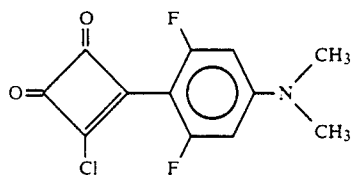

Figure 4:
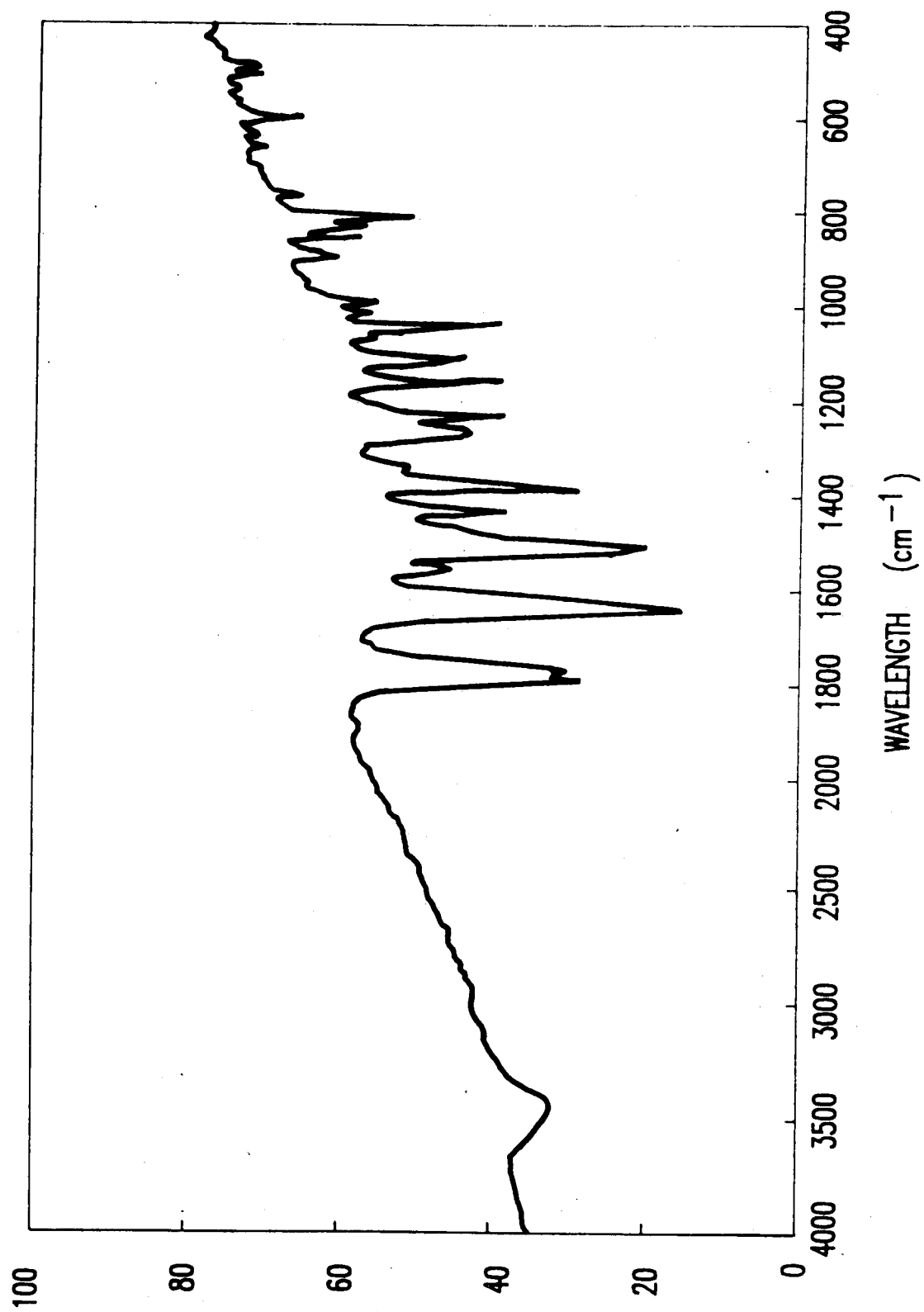
FIG. 4 is a graph showing the infrared absorption spectra of the cyclobutenedione compound obtained in Example 14.

The infrared absorption spectra of the compound are shown in FIG. 4. The ultraviolet absorption wavelength (maximum) UV(CH$_2$Cl$_2$) was 396 nm. Also, the elemental analysis of the compound for C$_{12}$H$_8$ClF$_2$NO$_2$ was as follows.

|   | Calculated (%) | Found (%) |
|---|---|---|
| C | 53.06 | 52.94 |
| H | 2.97 | 2.81 |
| N | 5.16 | 5.18 |

EXAMPLE 15

To 2.01 g (7.40 mmol) of the chlorocyclobutenedione compound obtained in Example 14 were added 10 ml of acetic acid and 5 ml of water, followed by refluxing for 2 hours. The reaction mixture was then allowed to cool, and precipitates deposited were collected by filtration to provide 1.61 g (yield 86%) of the hydroxycyclobutenedione compound shown by the following formula. Melting point was 223° C. (decomposed).

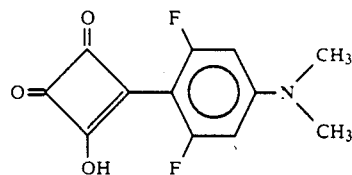

Figure 5:
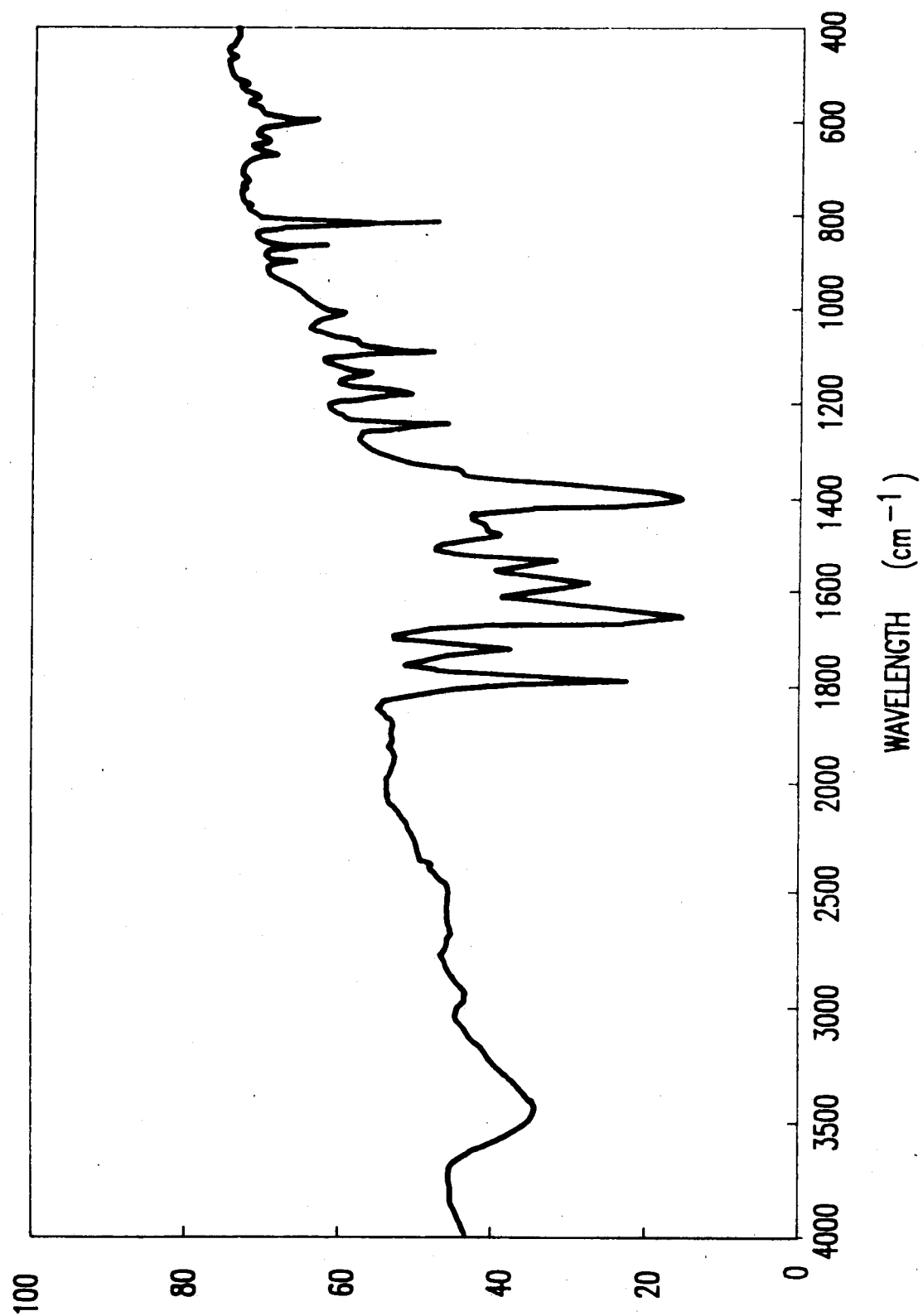
FIG. 5 is a graph showing the infrared absorption spectra of the cyclobutenedione compound obtained in Example 15.

The infrared absorption spectra of the compound are shown in FIG. 5. The ultraviolet absorption wavelengths (maximum) UV(CH$_2$Cl$_2$) were 355 nm. and 409 nm. Also, the elemental analysis of the compound for C$_{12}$H$_9$F$_2$NO$_3$ was as follows.

|   | Calculated (%) | Found (%) |
|---|---|---|
| C | 56.92 | 56.65 |
| H | 3.58 | 3.60 |
| N | 5.53 | 5.53 |

EXAMPLES 16 to 18

By following the same procedure as in Example 14 while changing the corresponding raw materials, 3,4-dichloro-3-cyclobutene-1,2-dione was reacted to provide the compounds shown in Table 4. The ultraviolet absorption wavelengths (maximum) thereof are also shown in Table 4.

TABLE 4

| Example No. | Desired Compound | UV (CH$_2$Cl$_2$) (nm) |
|---|---|---|
| 16 | (structure with C$_2$H$_5$ groups) | 398 |
| 17 | (structure with C$_3$H$_7$ groups) | 399 |
| 18 | (structure with C$_4$H$_9$ groups) | 400 |

EXAMPLES 19 to 21

By treating the compounds obtained in Examples 16 to 18 as in Example 15, the compounds shown in Table 5 were prepared. The ultraviolet absorption wavelengths thereof are also shown in Table 5.

TABLE 5

| Example No. | Desired Compound | UV (CH$_2$Cl$_2$) (nm) |
|---|---|---|
| 19 | (structure with C$_2$H$_5$ groups) | 357, 410 |
| 20 | (structure with C$_3$H$_7$ groups) | 359, 411 |

TABLE 5-continued

| Example No. | Desired Compound | UV (CH$_2$Cl$_2$) (nm) |
|---|---|---|
| 21 | (structure: cyclobutenedione with 2,6-difluoro-4-(N,N-dibutylamino)phenyl and OH) | 360 411 |

The following examples show on the cyclobutenedione derivative shown by formula (V) described above.

EXAMPLE 22

In 20 ml of methylene chloride were dissolved 1.93 g (12.8 mmol) of 3,4-dichloro-3-cyclobutene-1,2-dione and 4.52 g (25.4 mmol) of 3-acetylamino-N,N-dimethylaniline, and the solution was stirred for 2 hours at room temperature to perform reaction. After the reaction was over, the reaction mixture was washed with diluted hydrochloric acid and then with water, and separated and purified using column chromatography to provide 2.16 g (yield 58%) of a chlorocyclobutenedione compound shown by the following formula. Melting point: 218° C.

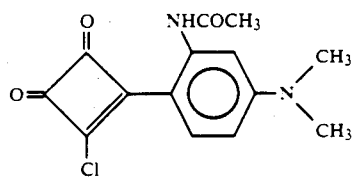

Figure 6:
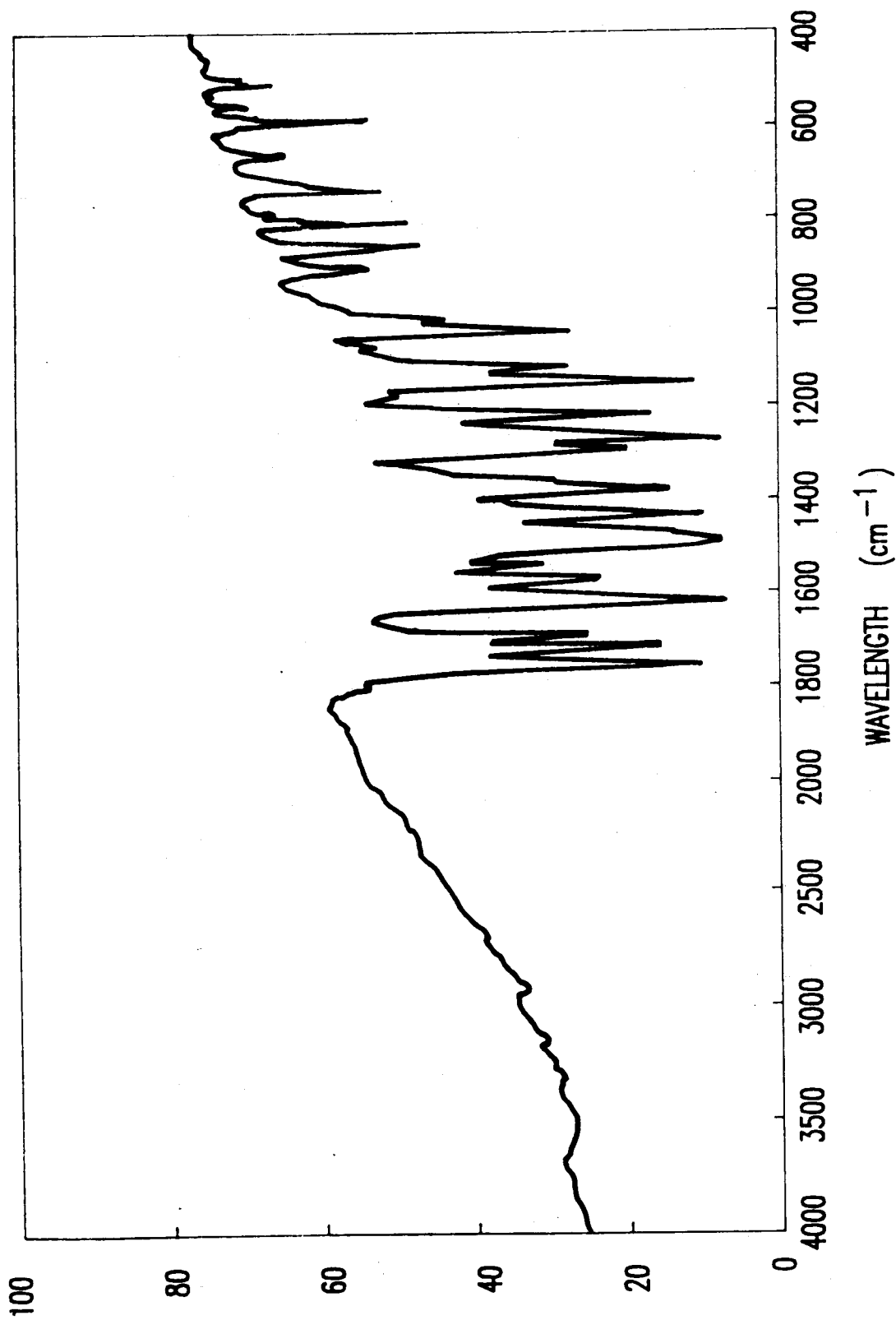
FIG. 6 is a graph showing the infrared absorption spectra of the cyclobutenedione derivative obtained in Example 22.

The infrared absorption spectra of the compound are shown in FIG. 6. The ultraviolet absorption wavelength (maximum) UV(CH$_2$Cl$_2$) was 434 nm. Also, the elemental analysis of the compound for C$_{14}$H$_{13}$ClN$_2$O$_3$ is as follows.

|  | Calculated (%) | Found (%) |
|---|---|---|
| C | 57.45 | 57.27 |
| H | 4.48 | 4.36 |
| N | 9.57 | 9.75 |

EXAMPLE 23

After adding 10 ml of acetic acid and 1 ml of water to 1.00 g (3.42 mmol) of the chlorocyclobutenedione compound obtained in Example 22, and refluxing for minutes, the reaction mixture was allowed to cool and precipitates thus deposited were collected by filtration to provide 0.86 g (yield 92%) of a hydroxybutenedione compound shown by the following formula. Melting point: 280° C. (decomposed).

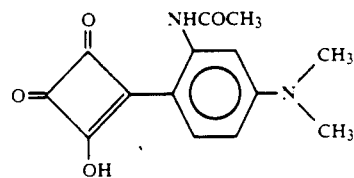

Figure 7:
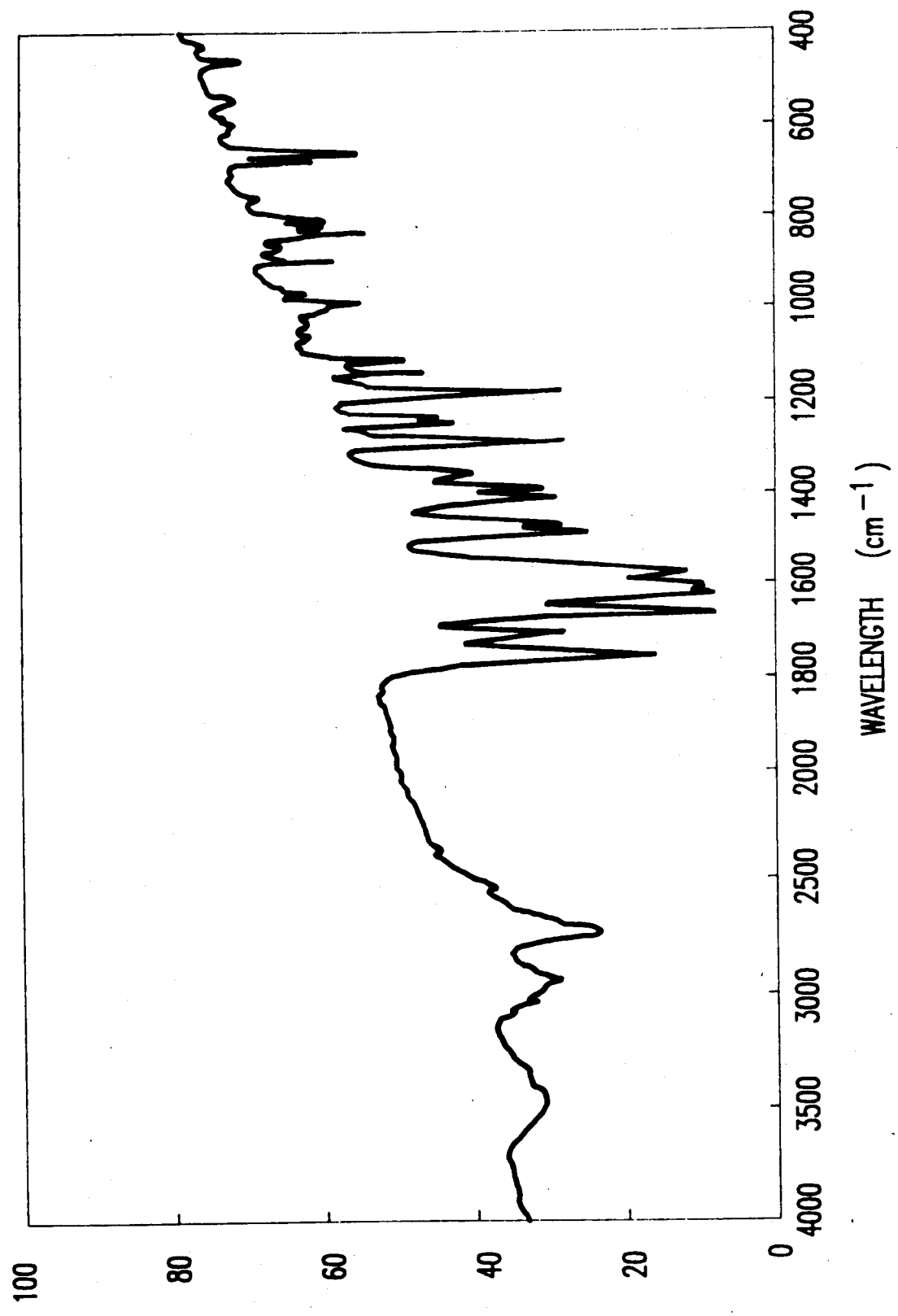
FIG. 7 is a graph showing the infrared absorption spectra of the cyclobutenedione derivative obtained in Example 23.

The infrared absorption spectra of the compound are shown in FIG. 7. The ultraviolet absorption wavelength (maximum) UV(CH$_2$Cl$_2$) was 415 nm. Also, the elemental analysis of the compound for C$_{14}$H$_{14}$N$_2$O$_4$ was as follows.

|  | Calculated (%) | Found (%) |
|---|---|---|
| C | 61.31 | 61.29 |
| H | 5.15 | 5.10 |
| N | 10.21 | 10.09 |

EXAMPLES 24 to 29

By following the same procedure as in Example 22 while selecting the corresponding raw materials, 3,4-dichlorpo-3-cyclobutene-1,2-dione was reacted as in Example 22 to provide the compounds shown in Table 6 below. The ultraviolet absorption wavelengths (maximum) of these compounds are also shown in Table 6.

TABLE 6

| Example No. | Desired Compound | UV (CH$_2$Cl$_2$) (nm) |
|---|---|---|
| 24 | (chlorocyclobutenedione with 2-NHCOCH$_3$, 4-N(C$_2$H$_5$)$_2$ phenyl) | 436 |
| 25 | (chlorocyclobutenedione with 2-NHCOCH$_3$, 4-N(C$_3$H$_7$)$_2$ phenyl) | 438 |
| 26 | (chlorocyclobutenedione with 2-NHCOCH$_3$, 4-N(C$_4$H$_9$)$_2$ phenyl) | 439 |
| 27 | (chlorocyclobutenedione with 2-NHCOC$_2$H$_5$, 4-N(CH$_3$)$_2$ phenyl) | 434 |
| 28 | (chlorocyclobutenedione with 2-NHCOC$_3$H$_7$, 4-N(CH$_3$)$_2$ phenyl) | 435 |

TABLE 6-continued

| Example No. | Desired Compound | UV (CH$_2$Cl$_2$) (nm) |
|---|---|---|
| 29 | (structure: cyclobutenedione with Cl, phenyl ring bearing NHCOC$_4$H$_9$ and N(CH$_3$)$_2$) | 435 |

EXAMPLES 30 to 35

By treating the compounds obtained in Examples 24 to 29 as in Example 23, the compounds shown in Table 7 were prepared. The ultraviolet absorption wavelengths (maximum) of these compounds are also shown in Table 7 below.

TABLE 7

| Example No. | Desired Compound | UV (CH$_2$Cl$_2$) (nm) |
|---|---|---|
| 30 | (structure with NHCOCH$_3$, N(C$_2$H$_5$)$_2$, OH) | 419 |
| 31 | (structure with NHCOCH$_3$, N(C$_3$H$_7$)$_2$, OH) | 423 |
| 32 | (structure with NHCOCH$_3$, N(C$_4$H$_9$)$_2$, OH) | 425 |
| 33 | (structure with NHCOC$_2$H$_5$, N(CH$_3$)$_2$, OH) | 416 |
| 34 | (structure with NHCOC$_3$H$_7$, N(CH$_3$)$_2$, OH) | 417 |
| 35 | (structure with NHCOC$_4$H$_9$, N(CH$_3$)$_2$, OH) | 417 |

Then, the following examples show on the cyclobutenedione derivative shown by formula (VI).

EXAMPLE 36

In 20 ml of methylene chloride were dissolved 1.16 g (7.68 mmol) of 3,4-dichloro-3-cyclobutene-1,2-dione, 3.00 g (15.4 mmol) of N-ethylcarbazole, 1.2 g (8.0 mmol) of boron trifluoride ethyl ether complex, and the solution was stirred for 24 hours at room temperature to perform reaction. After the reaction was over, the reaction mixture was washed with diluted hydrochloric acid and then with water, and separated and purified to provide a chlorocyclobutenedione compound shown by the following formula. The amount was 0.82 g (yield 34%) and the melting point was 216° to 217° C.

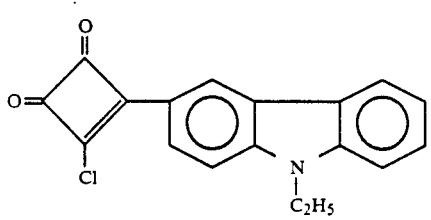

Figure 8:
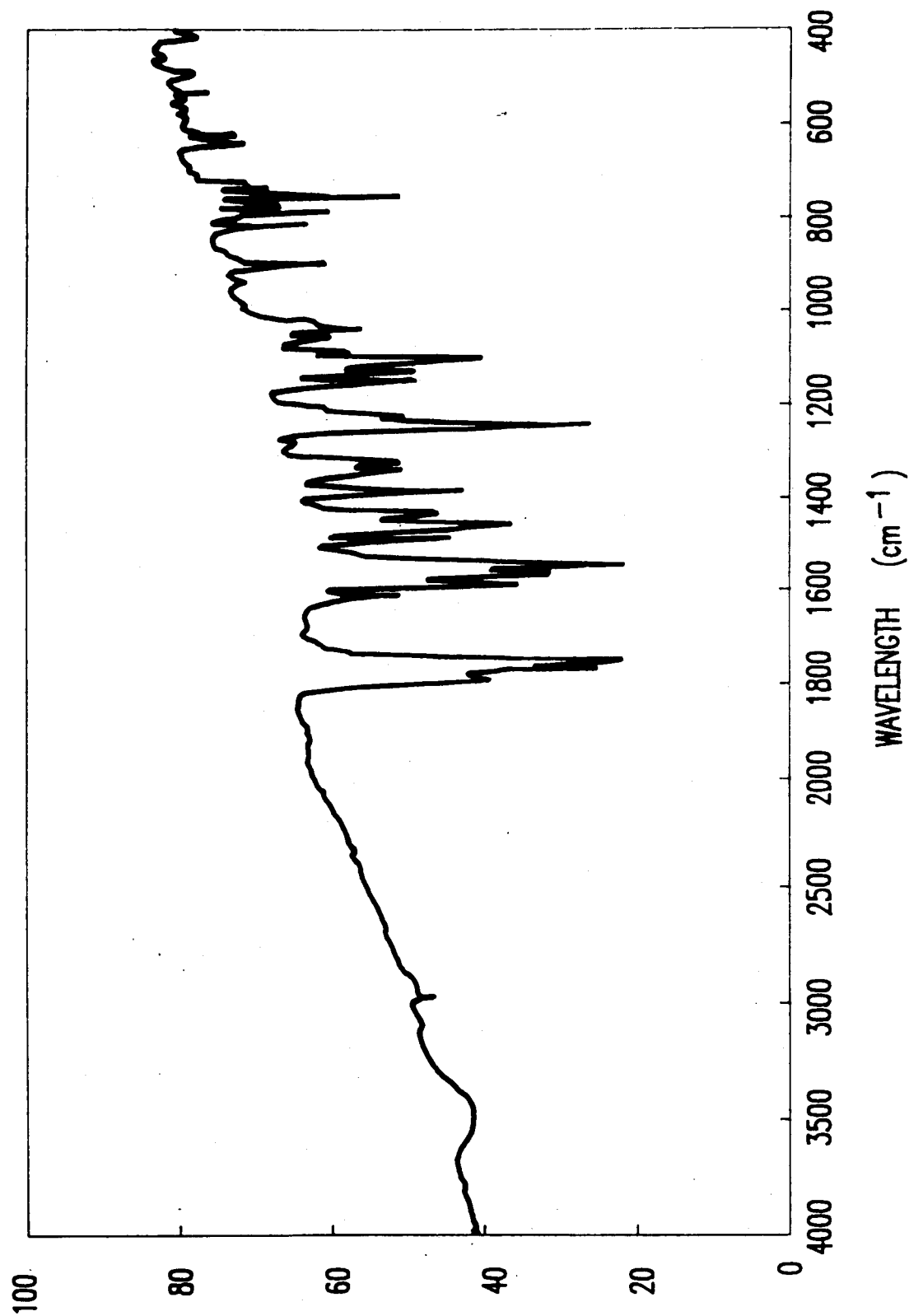
FIG. 8 is a graph showing the infrared absorption spectra of the cyclobutenedione derivative obtained in Example 36.

The infrared absorption spectra of the compound are shown in FIG. 8. The ultraviolet absorption wavelength (maximum) UV(CH$_2$Cl$_2$) was 395 nm. Also, the elemental analysis of the compound for C$_{18}$H$_{12}$ClNO$_2$ was as follows.

|   | Calculated (%) | Found (%) |
|---|---|---|
| C | 69.80 | 69.90 |
| H | 3.91 | 3.83 |
| N | 4.52 | 4.34 |

EXAMPLE 37

After adding 5 ml of acetic acid and 1 ml of water to 0.510 g (1.65 mmol) of the aforesaid chlorocyclobutenedione compound obtained in Example 36 and refluxing for 2 hours, the reaction mixture was allowed to cool and precipitates thus deposited were collected by filtration to provide 0.450 g (yield 94%) of a hydroxycyclobutenedione compound shown by the following formula. Melting point: 240° C. (decomposed).

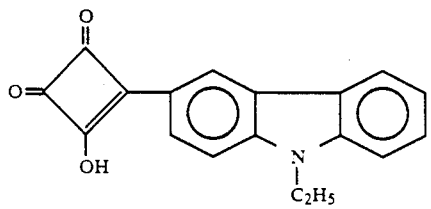

Figure 9:
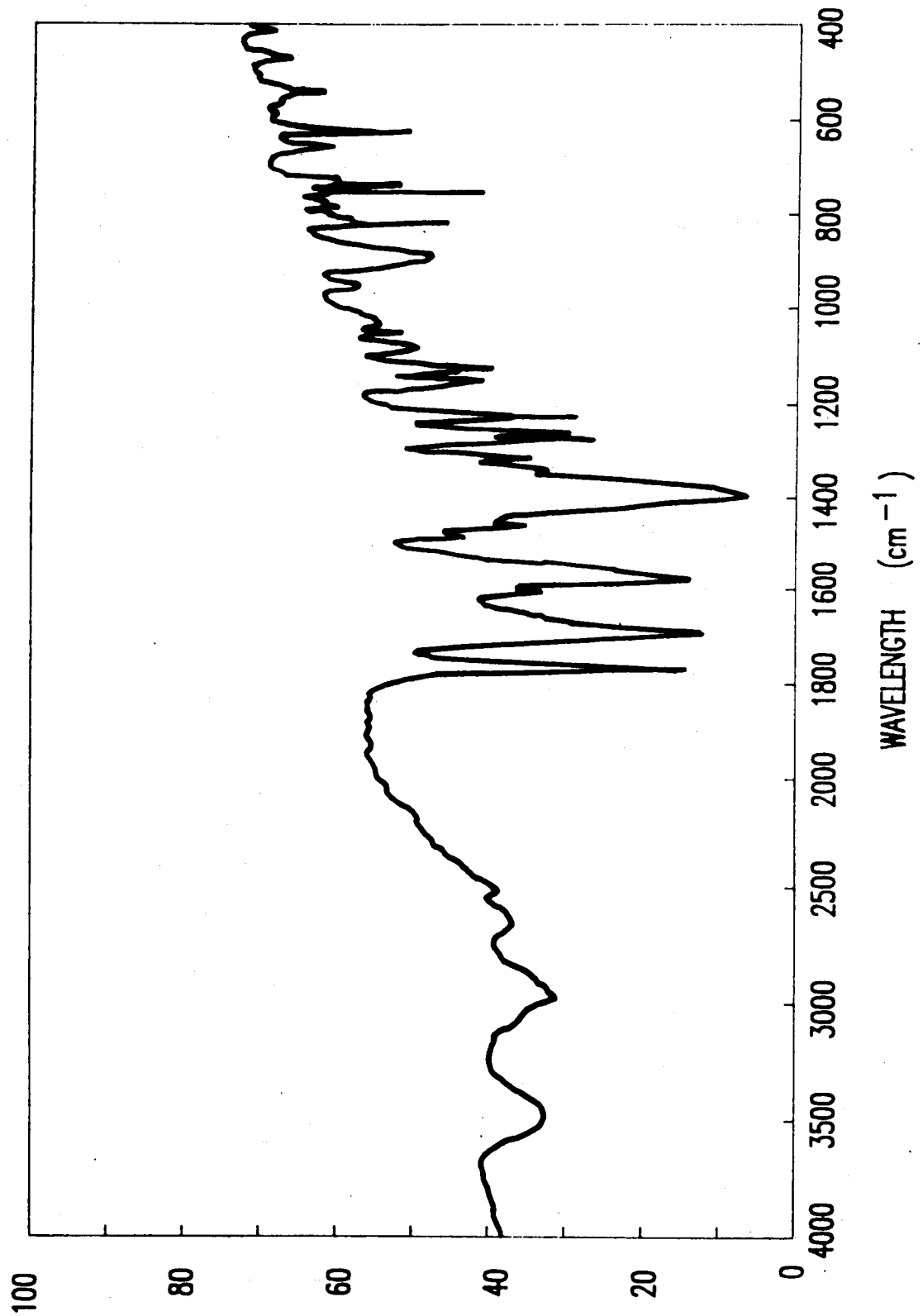
FIG. 9 is a graph showing the infrared absorption spectra of the cyclobutenedione derivative obtained in Example 37.

The infrared absorption spectra of the compound are shown in FIG. 9. The ultraviolet absorption wavelength (maximum) UV (CH$_2$Cl$_2$) was 373 nm. Also, the elemental analysis of the compound for C$_{18}$H$_{13}$NO$_3$ was as follows.

|   | Calculated (%) | Found (%) |
|---|---|---|
| C | 74.22 | 74.19 |
| H | 4.50 | 4.55 |

|   | Calculated (%) | Found (%) |
|---|---|---|
| N | 4.81 | 4.76 |

EXAMPLES 38 to 40

By following the same procedure as in Example 36 while selecting the corresponding raw materials, 3,4-dichloro-3-cyclobutene-1,2-dione was reacted as in Example 36 to provide the compounds shown in Table 8. The ultraviolet absorption wavelengths (maximum) thereof are also shown in Table 8.

TABLE 8

| Example No. | Desired Compound | UV ($CH_2Cl_2$) (nm) |
|---|---|---|
| 38 | (structure with Cl, N-$CH_3$) | 393 |
| 39 | (structure with Cl, N-$C_3H_7$) | 397 |
| 40 | (structure with Cl, N-$C_4H_9$) | 398 |

EXAMPLES 41 to 43

By treating the compounds obtained in Examples 38 to 40 as in Example 37, the compounds shown in Table 9 below were prepared. The ultraviolet absorption wavelengths (maximum) of these compounds are also shown in Table 9.

TABLE 9

| Example No. | Desired Compound | UV ($CH_2Cl_2$) (nm) |
|---|---|---|
| 41 | (structure with OH, N-$CH_3$) | 377 |
| 42 | (structure with OH, N-$C_3H_7$) | 380 |
| 43 | (structure with OH, N-$C_4H_9$) | 382 |

While the invention has been described in detail and with reference to specific embodiments thereof, it will be apparent to one skilled in the art that various changes and modifications can be made therein without departing from the spirit and scope thereof.

What is claimed is:

1. A squarylium compound represented by formula (II)

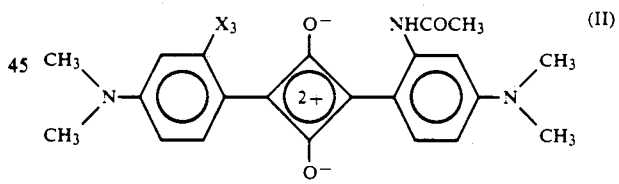

wherein $X_3$ is a hydrogen atom, a methyl group, a fluorine atom, or a hydroxy group.

* * * * *